United States Patent
Schachar et al.

(10) Patent No.: US 7,824,423 B2
(45) Date of Patent: *Nov. 2, 2010

(54) SYSTEM AND METHOD FOR MAKING INCISIONS FOR SCLERAL EYE IMPLANTS

(75) Inventors: Ronald A. Schachar, Dallas, TX (US); Donald P. Cudmore, Euless, TX (US)

(73) Assignee: Refocus Ocular, Inc., Dallas, TX (US)

( * ) Notice: Subject to any disclaimer, the term of this patent is extended or adjusted under 35 U.S.C. 154(b) by 1079 days.

This patent is subject to a terminal disclaimer.

(21) Appl. No.: 11/323,284

(22) Filed: Dec. 30, 2005

(65) Prior Publication Data

US 2006/0106409 A1    May 18, 2006

Related U.S. Application Data

(63) Continuation of application No. 10/080,877, filed on Feb. 22, 2002, now Pat. No. 7,189,248.

(60) Provisional application No. 60/271,028, filed on Feb. 23, 2001.

(51) Int. Cl.
*A61B 17/32*    (2006.01)
(52) U.S. Cl. .................. 606/166; 606/167; 606/180
(58) Field of Classification Search ............. 606/107, 606/159, 166, 167, 170, 180; 623/6.12
See application file for complete search history.

(56) References Cited

U.S. PATENT DOCUMENTS

| 3,609,864 A | 10/1971 | Bassett |
| 3,922,784 A | 12/1975 | Prince et al. |
| 4,052,988 A | 10/1977 | Doddi et al. |
| 4,071,029 A | 1/1978 | Richmond et al. |
| 4,340,059 A * | 7/1982 | Marinoff ............. 606/166 |
| 4,452,235 A | 6/1984 | Reynolds |

(Continued)

FOREIGN PATENT DOCUMENTS

EP    0 083 494 A1    12/1982

(Continued)

OTHER PUBLICATIONS

Translation of Office Action issued on Feb. 8, 2008 in Japanese Patent Application No. 2002-567203.

(Continued)

*Primary Examiner*—Darwin P Erezo

(57) ABSTRACT

A system and method is disclosed for making incisions in the sclera of an eye to form a scleral pocket to receive a scleral prosthesis. The system and method comprises a surgical tool comprising a surgical blade for making incisions in the sclera of an eye. When a surgeon places the surgical blade on the sclera of the eye a pressure sensor in the surgical tool determines whether there is sufficient pressure between the surgical tool and the sclera of the eye for the surgical tool to operate properly. The surgeon activates the surgical tool to cause the surgical blade to advance through the sclera to form an incision having dimensions to receive a scleral prosthesis. When the incision is complete the surgical blade is rotated back out of the incision. The incision has the exact dimensions to receive a scleral prosthesis.

18 Claims, 15 Drawing Sheets

U.S. PATENT DOCUMENTS

| | | | |
|---|---|---|---|
| 4,601,290 A * | 7/1986 | Effron et al. | 606/170 |
| 4,649,919 A | 3/1987 | Thimsen et al. | |
| 4,669,466 A | 6/1987 | L'Esperance | |
| 4,672,964 A | 6/1987 | Dee et al. | |
| 4,688,570 A | 8/1987 | Kramer et al. | |
| 4,753,655 A | 6/1988 | Hecht | |
| 4,819,631 A | 4/1989 | Poley | |
| 4,955,882 A * | 9/1990 | Hakky | 606/14 |
| 4,986,807 A * | 1/1991 | Farr | 604/22 |
| 5,006,123 A | 4/1991 | Soll et al. | |
| 5,090,955 A | 2/1992 | Simon | |
| 5,098,438 A * | 3/1992 | Siepser | 606/107 |
| 5,098,443 A | 3/1992 | Parel et al. | |
| 5,188,125 A * | 2/1993 | Kilmer et al. | 128/898 |
| 5,201,704 A | 4/1993 | Ray | |
| 5,203,865 A * | 4/1993 | Siepser | 606/166 |
| 5,215,104 A | 6/1993 | Steinert | |
| 5,222,959 A * | 6/1993 | Anis | 606/107 |
| 5,224,950 A | 7/1993 | Prywes | |
| 5,342,377 A | 8/1994 | Lazerson | |
| 5,423,841 A | 6/1995 | Kornefeld | |
| 5,431,671 A | 7/1995 | Nallakrishnan | |
| 5,441,510 A * | 8/1995 | Simpson et al. | 606/159 |
| 5,492,528 A | 2/1996 | Anis | |
| 5,522,829 A | 6/1996 | Michalos | |
| 5,547,468 A | 8/1996 | Simon et al. | |
| 5,571,106 A | 11/1996 | Coufal et al. | |
| 5,624,456 A | 4/1997 | Hellenkamp | |
| 5,651,782 A | 7/1997 | Simon et al. | |
| 5,779,723 A | 7/1998 | Schwind | |
| 5,817,115 A * | 10/1998 | Nigam | 606/166 |
| 5,908,433 A | 6/1999 | Eager et al. | |
| 6,007,578 A | 12/1999 | Schachar | |
| 6,033,437 A | 3/2000 | Perry | |
| 6,050,999 A | 4/2000 | Paraschac et al. | |
| 6,051,009 A | 4/2000 | Hellenkamp et al. | |
| 6,051,023 A | 4/2000 | Kilmer et al. | |
| 6,117,149 A | 9/2000 | Sorensen et al. | |
| 6,171,336 B1 | 1/2001 | Sawusch | |
| 6,231,583 B1 * | 5/2001 | Lee | 606/166 |
| 6,264,668 B1 | 7/2001 | Prywes | |
| 6,328,747 B1 | 12/2001 | Nun | |
| 6,358,262 B1 | 3/2002 | Chan et al. | |
| 6,443,966 B1 | 9/2002 | Shiu | |
| 6,565,584 B1 | 5/2003 | Mathis et al. | |
| 6,602,266 B1 | 8/2003 | Loomas et al. | |
| 6,605,093 B1 | 8/2003 | Blake | |
| 6,610,075 B1 | 8/2003 | Levesque et al. | |
| 6,692,524 B2 | 2/2004 | Baikoff | |
| 6,926,727 B2 * | 8/2005 | Schachar et al. | 606/166 |
| 7,189,248 B2 * | 3/2007 | Schachar et al. | 606/166 |
| 2002/0077642 A1 | 6/2002 | Patel et al. | |
| 2002/0116062 A1 | 8/2002 | Portney | |
| 2003/0120295 A1 | 6/2003 | Simpson et al. | |
| 2004/0073303 A1 | 4/2004 | Schanzlin et al. | |
| 2006/0106408 A1 | 5/2006 | Schachar et al. | |
| 2007/0078471 A1 | 4/2007 | Schachar et al. | |
| 2007/0123919 A1 | 5/2007 | Schachar et al. | |

FOREIGN PATENT DOCUMENTS

| | | |
|---|---|---|
| JP | 61170449 | 8/1986 |
| WO | WO 94/03129 A1 | 2/1994 |
| WO | WO 94/18636 A2 | 8/1994 |
| WO | WO 98/42409 A1 | 10/1998 |
| WO | WO 99/17684 A1 | 4/1999 |
| WO | WO 99/17691 A1 | 4/1999 |
| WO | WO 99/30645 A2 | 6/1999 |
| WO | WO 99/30656 A1 | 6/1999 |
| WO | WO 00/74600 A1 | 12/2000 |
| WO | WO 01/45607 A1 | 6/2001 |

OTHER PUBLICATIONS

The Surgical Armamentarium (American v. Mueller), 1980, pp. 4, Figure C.

Spencer P. Thornton, "Anterior Ciliary Sclerotomy (ACS), A Procedure to Reverse Presbyopia", Surgery for Hyperopia and Presbyopia, 1997, pp. 33-36.

Office Action dated Apr. 8, 2009 in connection with U.S. Appl. No. 11/606,480.

Office Action dated May 13, 2009 in connection with U.S. Appl. No. 11/698,008.

Michael R. Bryant et al., "Computer-Aided Surgical Design in Refractive Keratotomy", The CLAO Journal, vol. 13, No. 4, Jul. 1987, pp. 238-242.

Notification of Transmittal of the International Search Report or the Declaration dated Mar. 6, 2008 in PCT Application No. PCT/US03/15896.

Office Action dated Apr. 8, 2009 in connection with U.S. Appl. No. 11/606,480.

Office Action dated Nov. 2, 2009 in connection with U.S. Appl. No. 11/606,480.

Office Action dated Nov. 17, 2009 in connection with U.S. Appl. No. 10/443,122.

Office Action dated Sep. 22, 2009 in connection with U.S. Appl. No. 11/323,283.

Office Action dated Jun. 10, 2010 in connection with U.S. Appl. No. 11/199,591.

* cited by examiner

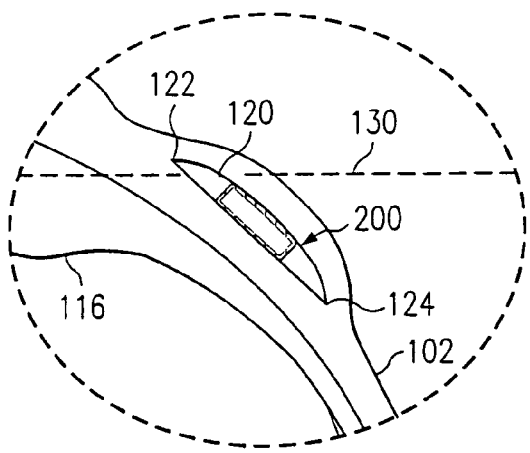
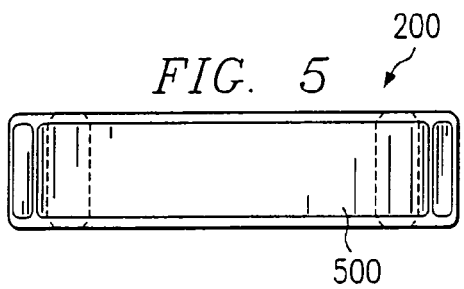
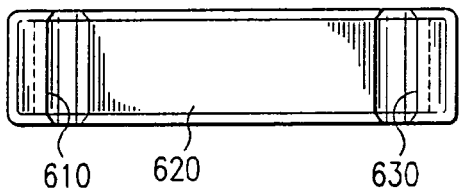
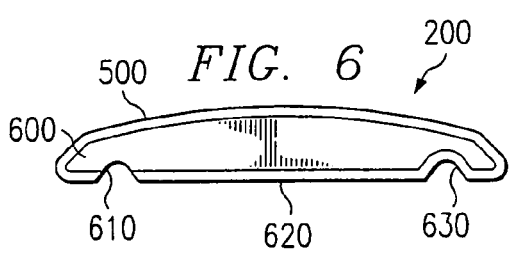
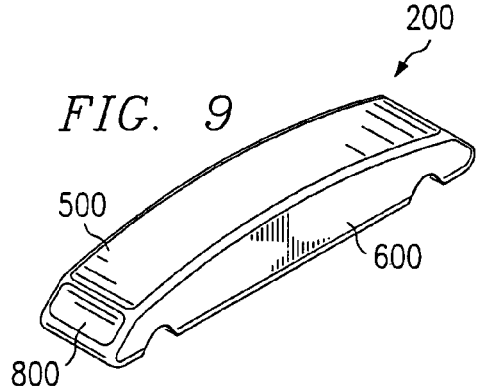
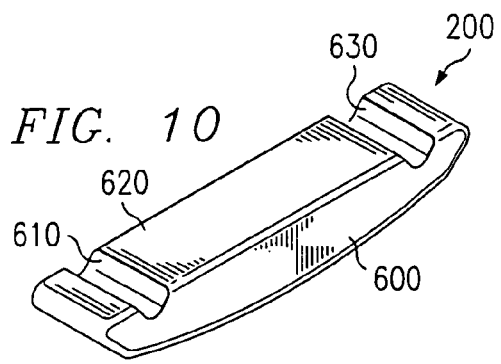

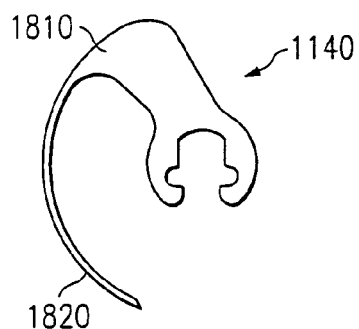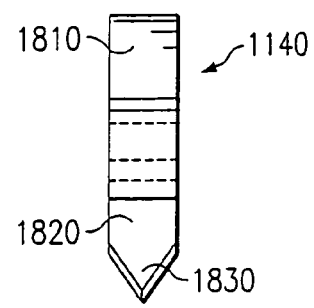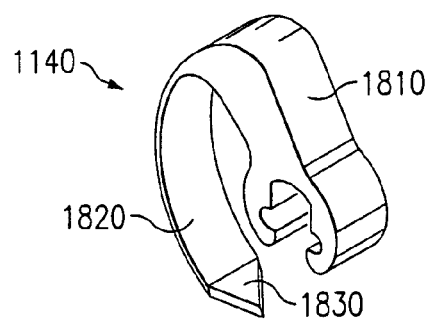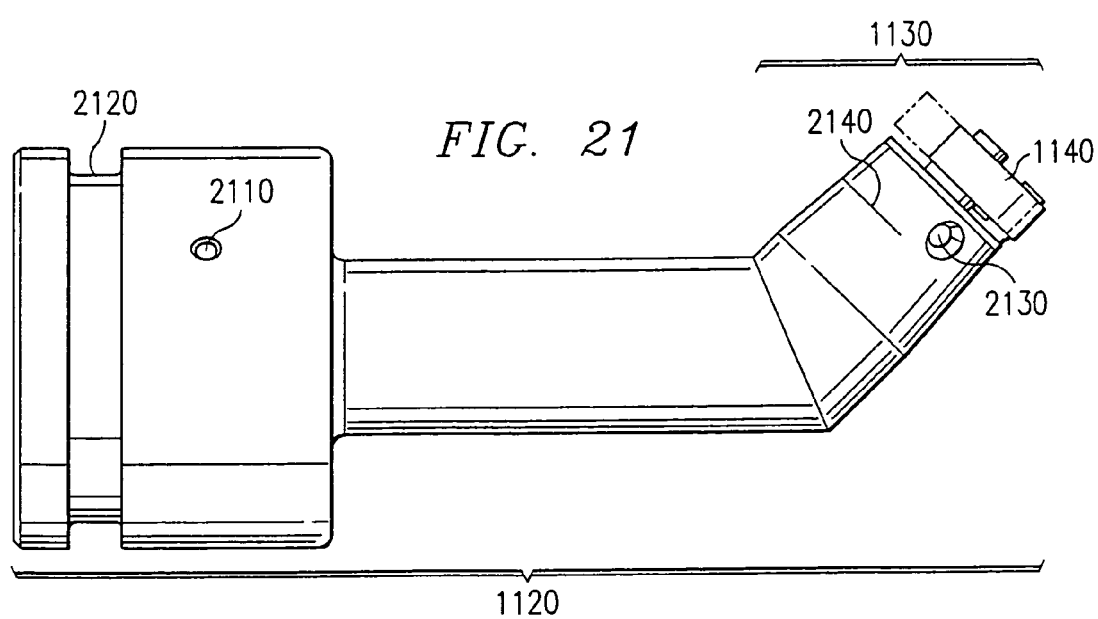

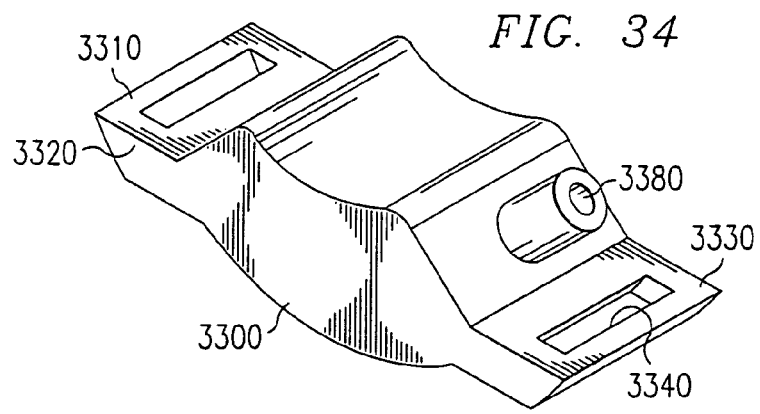
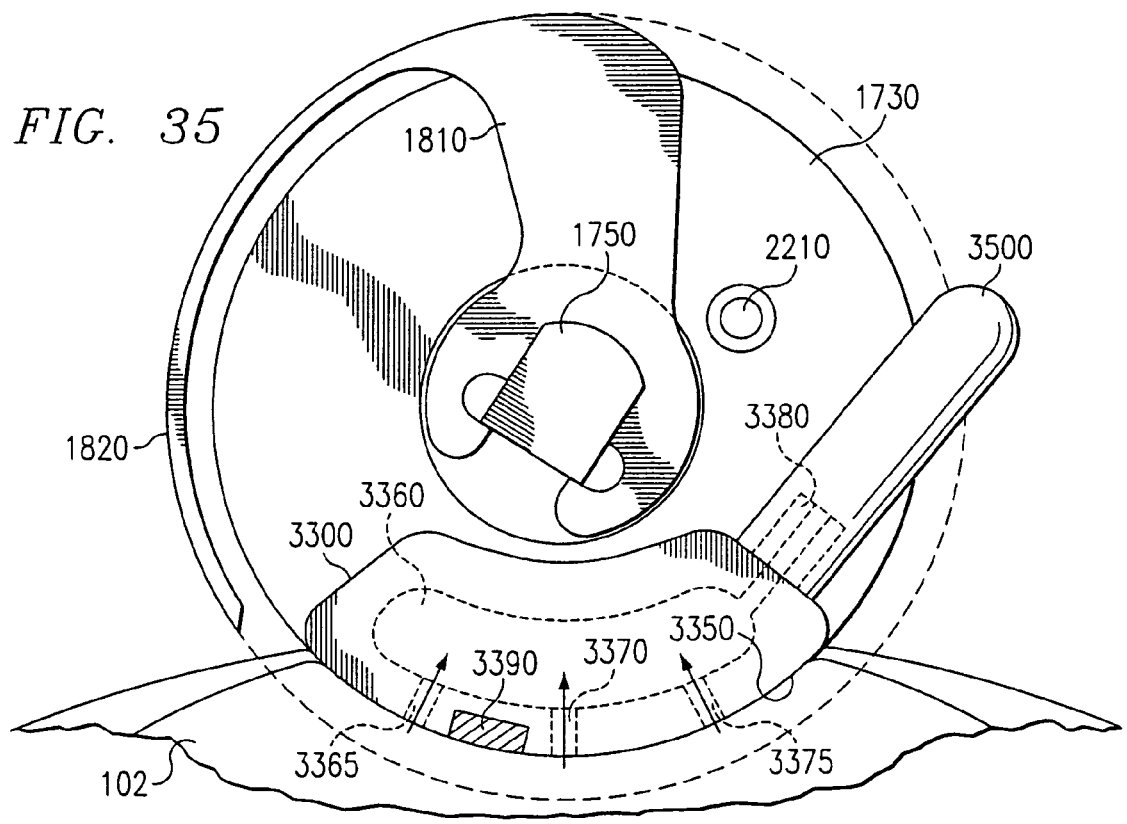

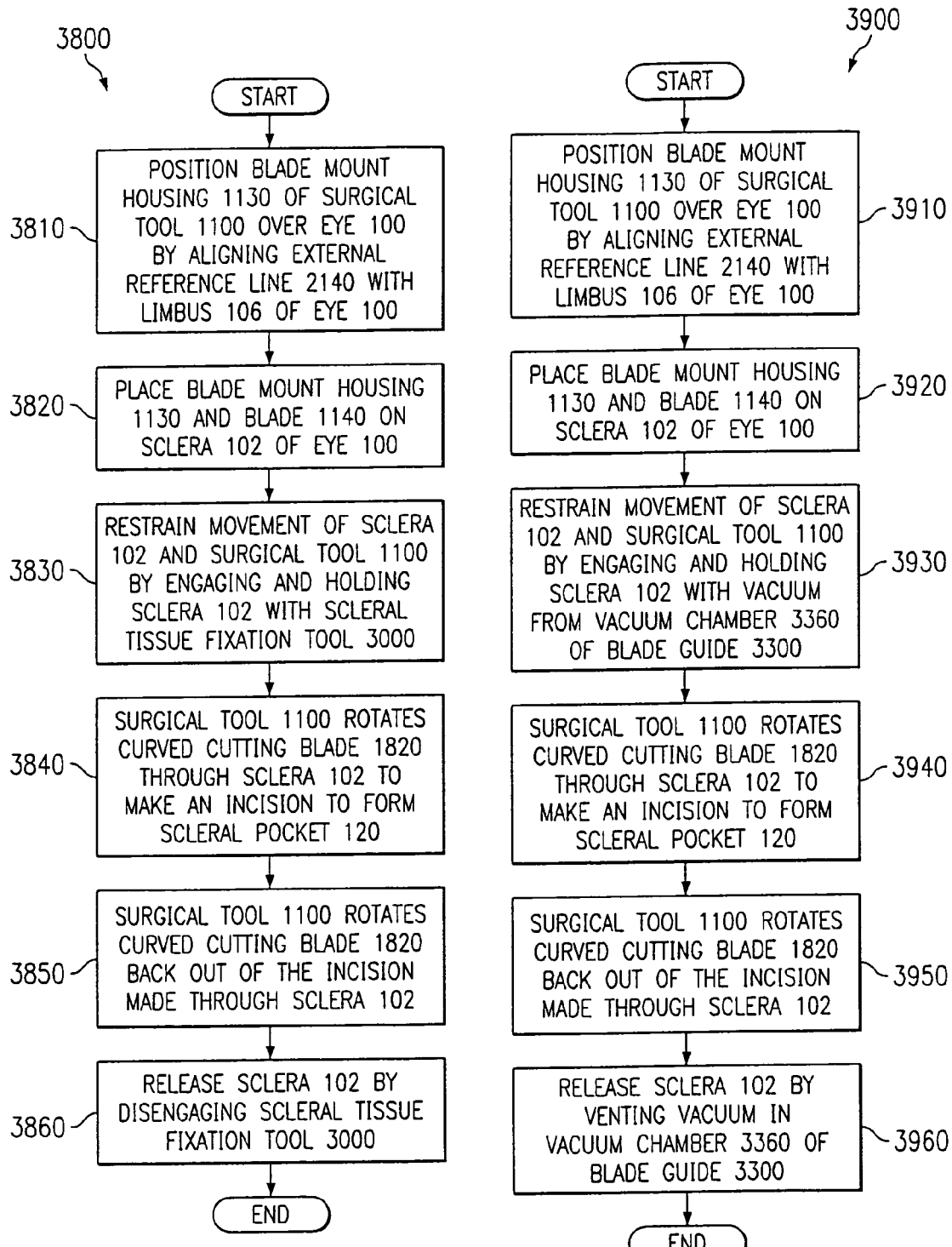

SYSTEM AND METHOD FOR MAKING INCISIONS FOR SCLERAL EYE IMPLANTS

PRIORITY CLAIM

This application is a continuation of U.S. patent application Ser. No. 10/080,877 filed on Feb. 22, 2002 (now U.S. Pat. No. 7,189,248), which claims priority to U.S. Provisional Patent Application Ser. No. 60/271,028 filed on Feb. 23, 2001.

CROSS-REFERENCE TO RELATED PATENT DOCUMENTS

The present disclosure is related to the inventions disclosed in the following United States patent applications and issued United States patents:

(1) U.S. Pat. No. 6,299,640 entitled "SCLERAL PROSTHESIS FOR TREATMENT OF PRESBYOPIA AND OTHER EYE DISORDERS" issued on Oct. 9, 2001;
(2) U.S. Pat. No. 6,197,056 entitled "SEGMENTED SCLERAL BAND FOR TREATMENT OF PRESBYOPIA AND OTHER EYE DISORDERS" issued on Mar. 6, 2001;
(3) U.S. Pat. No. 6,280,468 entitled "SCLERAL PROSTHESIS FOR TREATMENT OF PRESBYOPIA AND OTHER EYE DISORDERS" issued Aug. 28, 2001;
(4) U.S. Pat. No. 5,465,737 entitled "TREATMENT OF PRESBYOPIA AND OTHER EYE DISORDERS" issued on Nov. 14, 1995;
(5) U.S. Pat. No. 5,489,299 entitled "TREATMENT OF PRESBYOPIA AND OTHER EYE DISORDERS" issued on Feb. 6, 1996;
(6) U.S. Pat. No. 5,503,165 entitled "TREATMENT OF PRESBYOPIA AND OTHER EYE DISORDERS" issued on Apr. 2, 1996;
(7) U.S. Pat. No. 5,529,076 entitled "TREATMENT OF PRESBYOPIA AND OTHER EYE DISORDERS" issued on Jun. 25, 1996;
(8) U.S. Pat. No. 5,354,331 entitled "TREATMENT OF PRESBYOPIA AND OTHER EYE DISORDERS" issued on Oct. 11, 1994; and
(9) U.S. Pat. No. 5,722,952 entitled "TREATMENT OF PRESBYOPIA AND OTHER EYE DISORDERS" issued on Mar. 3, 1998;

which are commonly owned by the assignee of the present invention. The disclosures of these related United States patent applications and issued United States patents (collectively referred to hereafter as the "Presbyopia and Related Eye Disorder Patent Documents") are incorporated herein by reference for all purposes as if fully set forth herein.

FIELD OF THE INVENTION

The present invention relates generally to the treatment of presbyopia, hyperopia, primary open angle glaucoma, ocular hypertension and other similar eye disorders. The present invention comprises a system and method for making incisions within the sclera of an eye for the eye to receive a scleral prosthesis. Scleral prostheses are capable of increasing the amplitude of accommodation of the eye by increasing the effective working range of the ciliary muscle of the eye.

BACKGROUND OF THE INVENTION

In order for the human eye to have clear vision of objects at different distances, the effective focal length of the eye must be adjusted to keep the image of the object focused as sharply as possible on the retina. This change in effective focal length is known as accommodation and is accomplished in the eye by varying the shape of the crystalline lens. Generally, in the unaccommodated emmetropic eye the curvature of the lens is such that distant objects are sharply imaged on the retina. In the unaccommodated eye near objects are not focused sharply on the retina because their images lie behind the retinal surface. In order to visualize a near object clearly, the curvature of the crystalline lens is increased, thereby increasing its refractive power and causing the image of the near object to fall on the retina.

The change in shape of the crystalline lens is accomplished by the action of certain muscles and structures within the eyeball or globe of the eye. The lens is located in the forward part of the eye, immediately behind the pupil. It has the shape of a classical biconvex optical lens, i.e., it has a generally circular cross section having two convex refracting surfaces, and is located generally on the optical axis of the eye, i.e., a straight line drawn from the center of the cornea to the macula in the retina at the posterior portion of the globe. In the unaccommodated human eye the curvature of the posterior surface of the lens, i.e., the surface adjacent to the vitreous body, is somewhat greater than that of the anterior surface. The lens is closely surrounded by a membranous capsule that serves as an intermediate structure in the support and actuation of the lens. The lens and its capsule are suspended on the optical axis behind the pupil by a circular assembly of very many radially directed elastic fibers, the zonules, which are attached at their inner ends to the lens capsule and at their outer ends to the ciliary body and indirectly to the ciliary muscle, a muscular ring of tissue, located just within the outer supporting structure of the eye, the sclera. The ciliary muscle is relaxed in the unaccommodated eye and therefore assumes its largest diameter. According to the classical theory of accommodation, originating with Helmholtz, the relatively large diameter of the ciliary muscle in this condition causes a tension on the zonules which in turn pulls radially outward on the lens capsule, causing the equatorial diameter of the lens to increase slightly and decreasing the anterior-posterior dimension of the lens at the optical axis. Thus, the tension on the lens capsule causes the lens to assume a flattened state wherein the curvature of the anterior surface, and to some extent the posterior surface, is less than it would be in the absence of the tension. In this state the refractive power of the lens is relatively low and the eye is focused for clear vision for distant objects.

When the eye is intended to be focused on a near object, the ciliary muscles contract. According to the classical theory, this contraction causes the ciliary muscle to move forward and inward, thereby relaxing the outward pull of the zonules on the equator of the lens capsule. This reduced zonular tension allows the elastic capsule of the lens to contract causing an increase in the anterior-posterior diameter of the lens (i.e., the lens becomes more spherical) resulting in an increase in the optical power of the lens. Because of topographical differences in the thickness of the lens capsule, the central anterior radius of curvature decreases more than the central posterior radius of curvature. This is the accommodated condition of the eye wherein the image of near objects falls sharply on the retina.

Presbyopia is the universal decrease in the amplitude of accommodation that is typically observed in individuals over forty years of age. In the person having normal vision, i.e., having emmetropic eyes, the ability to focus on near objects is gradually lost, and the individual comes to need glasses for tasks requiring near vision, such as reading.

According to the conventional view the amplitude of accommodation of the aging eye is decreased because of the loss of elasticity of the lens capsule and/or sclerosis of the lens with age. Consequently, even though the radial tension on the zonules is relaxed by contraction of the ciliary muscles, the lens does not assume a greater curvature. According to the conventional view, it is not possible by any treatment to restore the accommodative power to the presbyopic eye. The loss of elasticity of the lens and capsule is seen as irreversible, and the only solution to the problems presented by presbyopia is to use corrective lenses for close work, or bifocal lenses, if corrective lenses are also required for distant vision.

Contrary to the conventional view, it is possible to restore the accommodative power to a presbyopic eye by implanting a plurality of scleral prostheses within the sclera of the eye. For each individual scleral prosthesis an incision is made in the sclera of the globe of the eye near the plane of the equator of the crystalline lens. The incision is then extended under the surface of the sclera to form a scleral "pocket." The scleral prosthesis is then placed within the pocket. A typical scleral prosthesis comprises a generally rectangularly shaped bar approximately five millimeters (5.0 mm) long, one and one half millimeters (1.5 mm) wide, and one millimeter (1.0 mm) tall. The anterior edge of the scleral prosthesis applies an outward force on the anterior edge of the scleral pocket which elevates the anterior portion of the sclera attached thereto and the ciliary body immediately beneath the sclera to increase the working distance of the ciliary muscle. This method is described more fully in the A Presbyopia and Related Eye Disorder Patent Documents that have been incorporated by reference into this patent document.

A physician who makes the incisions to form a scleral pocket must be a very skilled surgeon. The surgeon must use great care to ensure that the incisions are made properly. The incisions that must be made to form a scleral pocket are quite small. The incisions must be made at precisely the correct depth. The width and length of the scleral pocket must also be formed by precise incisions.

It is well known that physicians may differ significantly with respect to the level of surgical skill that they possess. Physicians who practice surgery regularly generally become quite skilled. Other physicians who do not practice surgery regularly are less skilled. Even skilled surgeons may find it difficult to make the precise incisions that are required to correctly form a scleral pocket.

If scleral pocket incisions are not made with sufficient precision the resulting scleral pocket will not be able to correctly support a scleral prosthesis. An incorrectly supported scleral prosthesis is not able to provide an acceptable level of vision correction.

It would be desirable if a system and method existed that would allow a surgeon to make the precise incisions that are required to form a scleral pocket. Accordingly, a need exists in the art for a system and method that is capable of making the precise incisions within the sclera of an eye to form a scleral pocket to receive a scleral prosthesis.

SUMMARY OF THE INVENTION

The system and method of the present invention comprises a surgical tool that is capable of making incisions within the sclera of an eye to form a scleral pocket to receive a scleral prosthesis.

An advantageous embodiment of the surgical tool of the present invention comprises a base housing and a drive shaft housing. The base housing of the surgical tool receives electrical power and control signals from an external surgical tool controller. The drive shaft housing comprises a blade mount housing that is mounted on the drive shaft housing at an angle to a central axis of the drive shaft housing. A surgical blade for making incisions in the sclera of an eye is mounted on the blade mount housing.

A surgeon positions the surgical blade of the surgical tool over the sclera of an eye by aligning an external reference line on the blade mount housing with the limbus of the eye. The surgeon then places the blade mount housing on the sclera of the eye. A pressure sensor determines when there is sufficient pressure between the surgical tool and the sclera of the eye for the surgical tool to operate properly. When the pressure sensor detects sufficient pressure the surgical tool may be activated. The surgeon sends an activation signal to the surgical tool to cause the surgical blade to advance through the sclera to form an incision having dimensions to receive a scleral prosthesis. The sclera of the eye and the surgical tool are restrained from moving while the surgical blade is moved through the sclera to make an incision. When the incision is complete the surgical blade is moved back out of the incision. The incision then has the exact dimensions to receive a scleral prosthesis.

It is an object of the invention to provide a surgical tool that is capable of making precise incisions in the sclera of an eye to create a scleral pocket that has exact dimensions to receive a scleral prosthesis.

It is an additional object of the invention to provide a surgical tool controller for controlling the operation of a surgical blade of a surgical tool for making incisions in the sclera of an eye to create a scleral pocket.

It is yet another object of the invention to provide an improved surgical blade for making incisions in the sclera of an eye to create a scleral pocket.

It is also another object of the present invention to provide an improved blade guide for guiding the motion of a surgical blade in the surgical tool of the present invention.

It is a further object of the present invention to provide a scleral tissue fixation tool that is capable of restraining the movement of the sclera of the eye away from the surgical blade of the surgical tool of the present invention when an incision is being made in the sclera of the eye.

It is another object of the present invention to provide a vacuum operated blade guide that is capable of restraining the movement of the sclera of the eye away from the surgical blade of the surgical tool of the present invention by applying a vacuum to the surface of the sclera of the eye.

It is yet another object of the present invention to provide an improved surgical blade of the surgical tool of the present invention that is capable of implanting a scleral prosthesis in a scleral pocket of an eye.

Additional objects of the present invention will become apparent from the description of the invention that follows.

The foregoing has outlined rather broadly the features and technical advantages of the present invention so that those skilled in the art may better understand the Detailed Description of the Invention that follows. Additional features and advantages of the invention will be described hereinafter that form the subject matter of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description of the Invention, it may be advantageous to set forth definitions of certain words and phrases used throughout this patent document. The terms "include" and "comprise," and derivatives thereof, mean inclusion without limitation; the term "or" is inclusive, meaning "and/or"; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, to bound to or with, have, have a property of, or the like; and the term "controller," "processor," or "apparatus" means any device, system or part thereof that controls at least one operation. Such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document. Those of ordinary skill should understand that in many instances (if not in most instances), such definitions apply to prior uses, as well as to future uses, of such defined words and phrases.

BRIEF DESCRIPTION OF THE DRAWINGS

FIG. 4 shows an enlarged view of the cross section of FIG. 3 in the region indicated by the circle 4;

FIG. 5 shows a top plan view of an exemplary scleral prosthesis;

FIG. 6 shows a front elevational view of the scleral prosthesis shown in FIG. 5 showing the contoured profile of the prosthesis and two notches in the bottom of the prosthesis;

FIG. 7 shows a bottom plan view of the scleral prosthesis shown in FIG. 5 showing the location of two notches in the bottom of the prosthesis;

FIG. 8 shows an end view of the scleral prosthesis shown in FIG. 5;

FIG. 9 shows a top perspective view of the scleral prosthesis shown in FIG. 5 showing the top and one side and one end of the prosthesis;

FIG. 10 shows a bottom perspective view of the scleral prosthesis shown in FIG. 5 showing the bottom and one side of the prosthesis;

FIG. 18 shows a top plan view of a blade of the surgical tool of the present invention;

FIG. 19 shows a side view of the blade shown in FIG. 18;

FIG. 20 shows a perspective view of the blade shown in FIG. 18;

FIG. 21 shows a side view of the drive shaft housing and the blade mount housing and the blade of the surgical tool of the present invention;

FIG. 34 shows a perspective view of the blade guide shown in FIG. 33;

FIG. 35 shows a side view of an alternative advantageous embodiment of a blade guide of the surgical tool of the present invention comprising an interior vacuum chamber showing the operation of the vacuum chamber blade guide;

FIG. 38 shows a flow chart of an advantageous embodiment of a method of the present invention for making incisions to form a scleral pocket for a scleral prosthesis;

FIG. 39 shows a flow chart of an alternate advantageous embodiment of a method of the present invention for making incisions to form a scleral pocket for a scleral prosthesis;

DETAILED DESCRIPTION OF THE INVENTION

Figure 1:
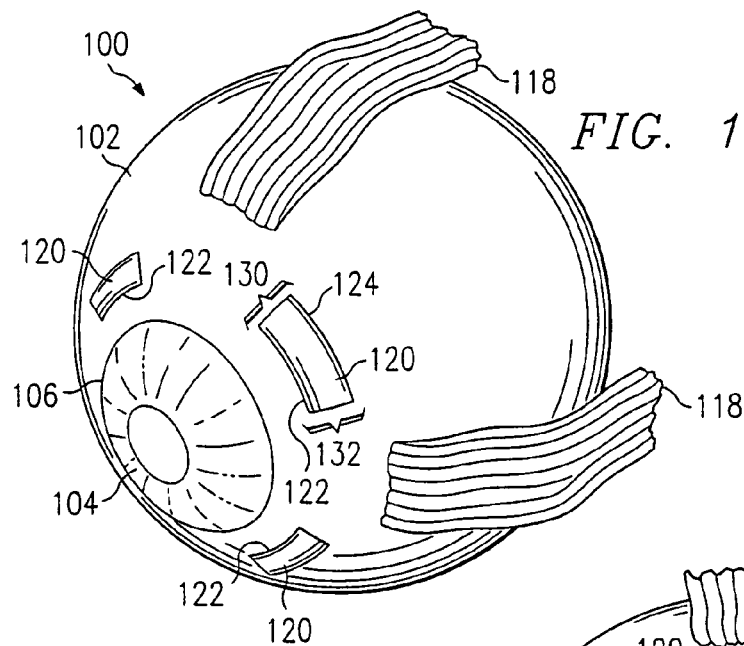
FIG. 1 shows an isometric view of an eye having scleral pockets for receiving scleral prostheses.

FIGS. 1 through 48, discussed below, and the various embodiments used to describe the principles of the present invention in this patent document are by way of illustration only and should not be construed in any way to limit the scope of the invention. Those skilled in the art will understand that the principles of the present invention may be implemented in any suitably arranged surgical tool and with any suitable surgical method.

The system and method of the present invention comprise a surgical tool that is capable of making incisions in the sclera of an eye in order for the eye to receive a scleral prosthesis. Scleral prostheses are used to treat presbyopia (and other similar eye disorders) by increasing the effective working distance of the ciliary muscle of the eye. This is accomplished by increasing the distance between the ciliary muscle and the lens equator by increasing the diameter of the sclera in the region of the ciliary body.

The effective working distance of the ciliary muscle is increased by implanting in pockets surgically formed in the sclera of the eye a plurality of scleral prostheses designed to place an outward traction on the sclera in the region of the ciliary body. The relevant anatomy of the eye for locating the scleral pockets may be seen by reference to FIGS. 1-4. The outermost layer of the eye 100 comprises the white, tough sclera 102 which encompasses most of the globe and the transparent cornea 104, which constitutes the anterior segment of the outer coat. The circular junction of the cornea and sclera is the limbus 106. Within the globe of the eye, as illustrated in the cross-section shown in FIG. 3, the crystalline lens 108 is enclosed in a thin membranous capsule and is located immediately posterior to the iris 112, suspended centrally posterior to the pupil 114 on the optical axis of the eye. The lens 108 is suspended by zonules 115 extending between the lens capsule at the equator 110 of the lens 108 and the ciliary body 116. The ciliary body 116 lies just under the sclera 102 (i.e., just inwardly of the sclera 102) and is attached to the inner surface of the sclera 102. As may be seen in FIG. 3, the ciliary body 116 lies generally in a plane 130 defined by the equator 110 of the lens 108. The plane 130 can also be extended to intersect the sclera 102 whereby it forms a generally circular intersection located about two (2) millimeters posterior to the limbus 106. The external muscles 118 of the eyeball control the movement of the eye.

A generally outwardly directed traction is exerted on the sclera in the region of the ciliary body to expand the sclera 102 in that region. This expansion of the sclera 102 produces a corresponding expansion of the attached ciliary body 116 and moves the ciliary body 116 outwardly away from the equator 110 of the lens 108, generally in the plane 130 of the equator 110 of the lens 108. The sclera 102 is preferably expanded approximately in the plane of the equator 110 of the lens 108. However, any expansion of the, sclera 102 in the region of the ciliary body 116, i.e., in the region of the sclera somewhat anterior or posterior to the plane of the equator 110 of the lens 108 is within the scope of the invention, provided that such expansion of the sclera 102 moves the ciliary body 116 away from the equator 110 of the lens 108. Typically, the expansion of the sclera will be accomplished in the region from about one and one half millimeters (1.5 mm) anterior to the plane 130 of the equator 110 of the lens 108 to about two and one half millimeters (2.5 mm) posterior to that plane, i.e., from about one half millimeter (0.5 mm) to about four and one half millimeters (4.5 mm) posterior to the limbus 106. Accordingly, the anterior margin 122 of a scleral pocket 120 will be located in that region of the sclera.

An exemplary scleral pocket 120 is illustrated in FIG. 1. An incision is made in the surface of sclera 120 along the line indicated with reference numeral 130. The incision is then extended under the surface of sclera 120 between the anterior margin 122 and the posterior margin 124 of scleral pocket 120. This forms a "pocket" under the surface of sclera 102. The incision may also be extended through the surface of sclera 102 along the line indicated with reference number 132. This forms a "belt loop" type structure in the surface of sclera 102. For convenience the "pocket" type structure and the "belt loop" type structure will both be referred to as scleral pocket 120.

Figure 3:
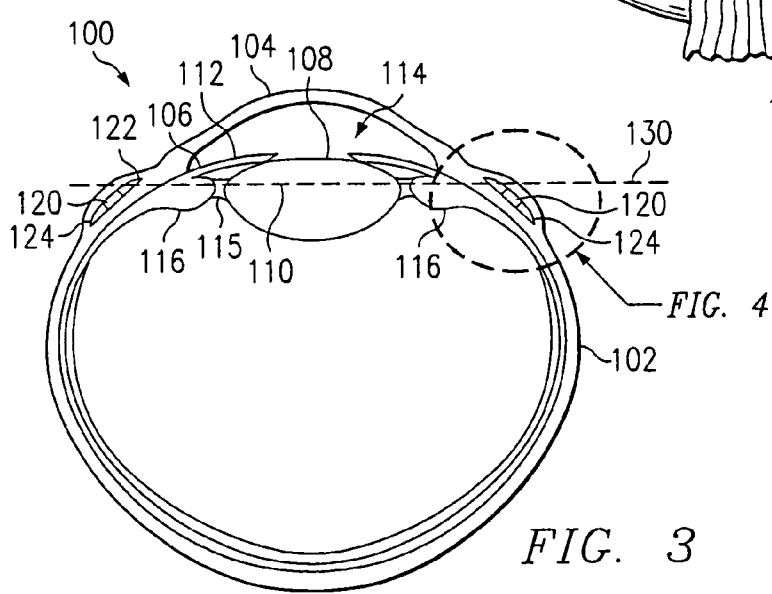
FIG. 3 shows a cross section of the eye of FIG. 2 along the line 3-3.

The scleral prosthesis 200 is designed to be placed within scleral pocket 120. Scleral prosthesis 200 within scleral pocket 120 applies an outwardly directed traction to the sclera 102 at the general position of the anterior margin 122 of the scleral pocket 120. The position of prosthesis 200 within scleral pocket 120 and its operation to expand the sclera are illustrated in FIGS. 3 and 4.

An advantageous embodiment of eye implant prosthesis 200 is illustrated in FIGS. 5-10. FIG. 5 shows a plan view of the top 500 of prosthesis 200. In one advantageous embodiment, the length of prosthesis 200 is approximately five thousand five hundred microns (5500 μm) or, equivalently, approximately five and one half millimeters (5.5 mm).

FIG. 6 shows a front elevational view of the prosthesis 200 of FIG. 5 showing one side 600 of prosthesis 200. In one advantageous embodiment, the maximum height of prosthesis 200 is approximately nine hundred twenty five microns (925 μm) or, equivalently, approximately nine hundred twenty five thousandths of a millimeter (0.925 mm). A first notch 610 is located in the base 620 of prosthesis 200 at a first end of prosthesis 200. A second notch 630 is located in the base 620 of prosthesis 200 at a second end of prosthesis 200. When prosthesis 200 is located within scleral pocket 120 intraocular pressure from the interior of eye 100 pushes scleral tissue into notch 610 and into notch 630. The presence of scleral tissue in notch 610 and in notch 630 provides an anchoring mechanism that tends to prevent movement of prosthesis 200.

FIG. 7 shows a plan view of the bottom 620 of prosthesis 200. Notch 610 and notch 630 extend across the bottom 620 of prosthesis 200.

FIG. 8 shows an end view of prosthesis 200 showing one end 800 of the prosthesis 200. In one advantageous embodiment, the width of prosthesis 200 is approximately one thousand three hundred eighty microns (1380 μm) or, equivalently, approximately one and three hundred eighty thousandths millimeter (1.380 mm).

FIG. 9 shows a perspective top view of prosthesis 200. FIG. 9 shows top 500, one side 600 and one end 800 of the prosthesis 200. FIG. 10 shows a perspective bottom view of prosthesis 200. FIG. 10 shows the bottom 620 (including notches 610 and 630) and one side 600 of prosthesis 200.

Other types of scleral prosthesis 200 may be used including those types of prosthesis disclosed in the "Presbyopia and Related Eye Disorder Patent Documents" previously incorporated by reference into this patent document.

Scleral prosthesis 200 is made of a material that is sufficiently rigid to exert a force on the sclera sufficient to produce the radial expansion required by the method of the invention and that is physiologically acceptable for long-term implantation or contact with the ocular tissues. Such materials are well-known in the surgical art and include suitable metals, ceramics, and synthetic resins. Suitable metals include titanium, gold, platinum, stainless steel, nitinol, tantalum and various surgically acceptable alloys, and the like. Suitable ceramics may include crystalline and vitreous materials such as porcelain, alumina, silica, silicon carbide, high-strength glasses and the like. Suitable synthetic materials include physiologically inert materials such as poly(methyl methacrylate), polyethylene, polypropylene, poly(tetrafluoroethylene), polycarbonate, silicone resins, hydrophilic plastics, hydrophobic plastics, hypoxy-appetite, and the like. The scleral prosthesis 200 may also be made of composite materials incorporating a synthetic resin or other matrix reinforced with fibers of high strength material such as glass fibers, boron fibers or the like. Thus, scleral prosthesis 200 may be made of glass-fiber-reinforced epoxy resin, carbon fiber-reinforced epoxy resin, carbon fiber-reinforced carbon. (carbon-carbon), or the like. Scleral prosthesis 200 may be made of a semi-rigid exterior and a liquid or gel filled interior so that the internal and external dimensions can be altered by injecting various amounts of liquid: water, saline, or silicone oil; or various amounts of a gel: silicone, collagen, or gelatin. The semi-rigid exterior may be made of any of the already listed materials. A preferred material for the entire scleral prosthesis 200 is surgical grade poly(methyl methacrylate). Scleral prosthesis 200 may also be made of a material that regains its shape when deformed such as a memory metal (e.g., nitinol).

Scleral prosthesis 200 may be manufactured by any conventional technique appropriate to the material used, such as machining, injection molding, heat molding, compression molding and the like.

Scleral prosthesis 200 may be foldable to facilitate insertion into a scleral belt loop or made in a plurality of parts so that it can be assembled prior to use or may be installed separately to form a complete prosthesis.

To implant scleral prosthesis 200 by hand, the surgeon locates the proper region of the sclera to be expanded by measuring a distance of preferably three and one half millimeters (3.5 mm) posterior of the limbus 106. At two millimeters (2.0 mm) clockwise and counterclockwise from each of the forty five degree (45°) meridians of the eye, and three and one half millimeters (3.5 mm) posterior to the limbus 106, partial scleral thickness parallel incisions, i.e., anterior-posterior incisions, are made which are one and one half millimeters (1.5 mm) long and three hundred fifty microns (350 μm) deep. Using a lamella blade the sclera is dissected until the partial thickness incisions are connected so that four scleral pockets or belt loops are made which have an anterior length of four millimeters (4.0 mm), and a length extending generally axially of the eye of one and one half millimeters (1.5 mm). Thus, each pocket or belt loop is preferably centered over the forty five degree (45°) meridian of the eye. A scleral prosthesis 200 is then inserted in each of the four scleral belt loops. This produces symmetrical scleral expansion which will produce the desired result of increasing the effective working distance of the ciliary muscle.

The location of the scleral prostheses 200 implanted in eye 100 is illustrated in FIGS. 1-4. FIG. 1 is an isometric view of an eye 100 having a globe with the relevant exterior anatomical parts indicated as discussed above.

Figure 2:
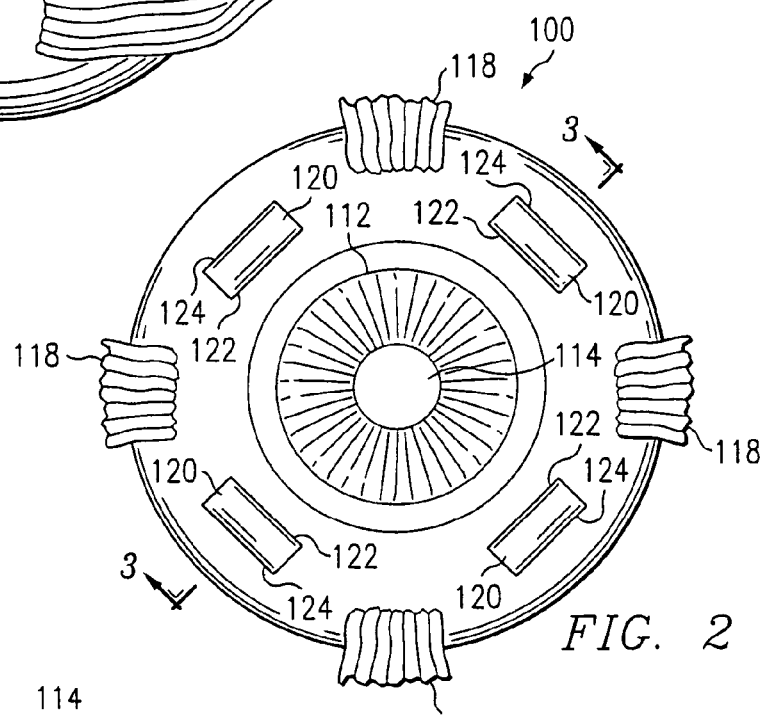
FIG. 2 shows a front elevational view of an eye showing the location of four straight scleral pockets.

FIG. 2 shows a front elevational view of an eye 100 showing the scleral pockets 120 formed at approximately the forty five degree (45°) meridians of the eye, i.e., approximately halfway between the vertical and horizontal meridians of the globe. This location is preferred because it avoids interference with structures of the eye that are located generally on the vertical and horizontal meridians. FIG. 2 shows the use of straight scleral pockets 120. Straight scleral pockets 120 are somewhat simpler to prepare surgically than curved scleral pockets (not shown). For many patients the use of straight scleral prostheses provide adequate treatment of presbyopia. Alternatively, curved scleral prostheses may be used as discussed in the "Presbyopia and Related Eye Disorder Patent Documents" previously incorporated by reference into this patent document.

FIG. 3 shows a cross-section of eye 100, taken along the line 3-3 in FIG. 2, showing the placement of scleral prosthesis 200 relative to the significant anatomical structures of the eye. FIG. 3 shows the general configuration of the scleral pockets 120 and the prostheses 200 of the type illustrated in FIGS. 5-10. The anterior margins 122 of the scleral pockets 120 are located approximately in the plane 130 of the equator 110 of the lens 108. The presence of prosthesis 200 causes the portion of the sclera anterior to the scleral pocket 120 to be expanded somewhat more than the posterior portion. This places the sclera anterior to the scleral pocket 120 under a radial tension and causes it to expand from its normal diameter at that position. This scleral expansion draws with it the underlying ciliary body 116 and causes the ciliary body to be drawn away from the equator 110 of the lens 108. Accordingly, the expansion of the ciliary body 116 operates to increase the working distance of the ciliary muscle and restore, at least in part, the ability of the eye to accommodate for clear focusing on objects at different distances.

FIG. 4 shows an enlarged portion of one of the scleral pockets 120 with adjacent anatomical structures. It shows the relation of the scleral pocket 120 to the underlying structures and its location just posterior to the equator of the lens 108 and overlying the ciliary body 116.

The surgical procedures described above to make incisions within the sclera 102 of eye 100 are done by hand. That is, the surgeon makes the incisions in sclera 102 that are required to form scleral pocket 120 using standard surgical tools such as a scalpel. The surgeon must be very skilled in the use of a scalpel to make incisions that have the required precision.

However, the system and method of the present invention provide a much more efficient and precise way to make the required incisions. The system and method of the present invention comprise a surgical tool that is specifically designed to make very precise incisions in the sclera 102 of an eye 100 to form a scleral pocket 120.

Figure 11:
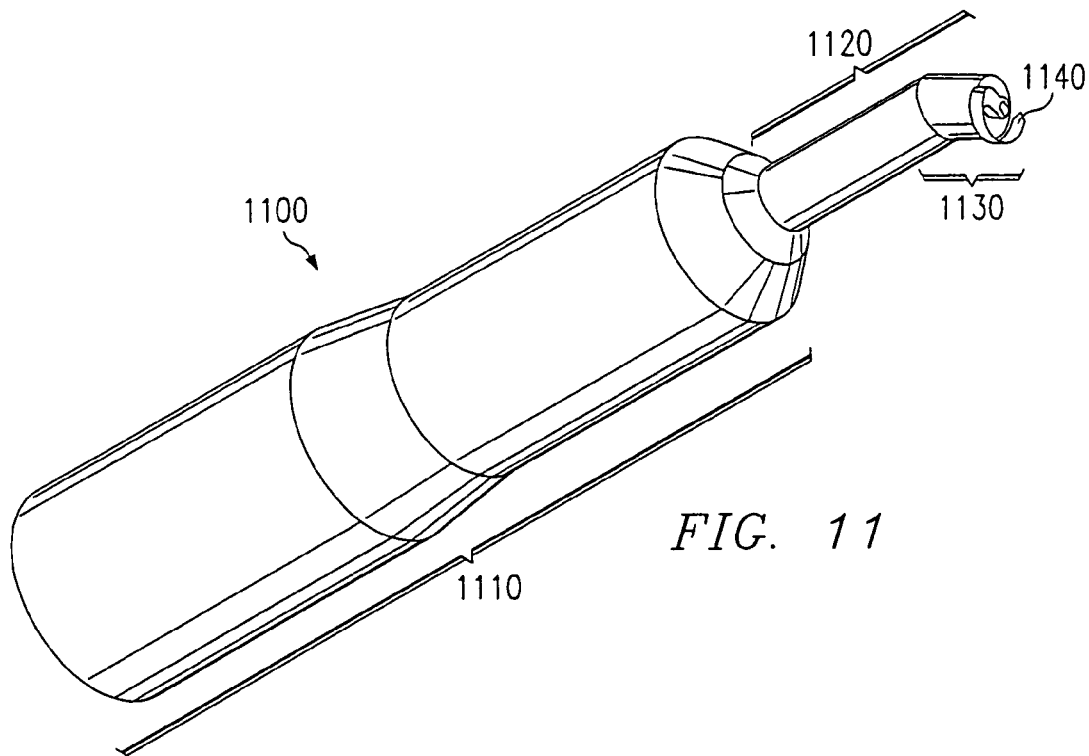
FIG. 11 shows a perspective view of a surgical tool constructed in accordance with the principles of the present invention for making incisions in the sclera of an eye to create a scleral pocket to receive a scleral prosthesis.

FIG. 11 shows a perspective view of an electromechanical surgical tool 1100 constructed in accordance with the principles of the present invention. As will be more fully described, surgical tool 1100 is capable of making incisions in eye 100 to create a scleral pocket 120 to receive a scleral prosthesis 200. Surgical tool 1100 comprises a base housing 1110 and a drive shaft housing 1120. Drive shaft housing 1120 comprises a blade mount housing 1130 that mounted on the drive shaft housing 1120 an angle to a central axis of drive shaft housing 1120. The reason for mounting blade mount housing 1130 at an angle with respect to the central axis of drive shaft housing 1120 is to facilitate the placement of blade mount housing 1130 on eye 100 during the surgical process. Lastly, blade 1140 is mounted on blade mount housing 1130.

Figure 12:
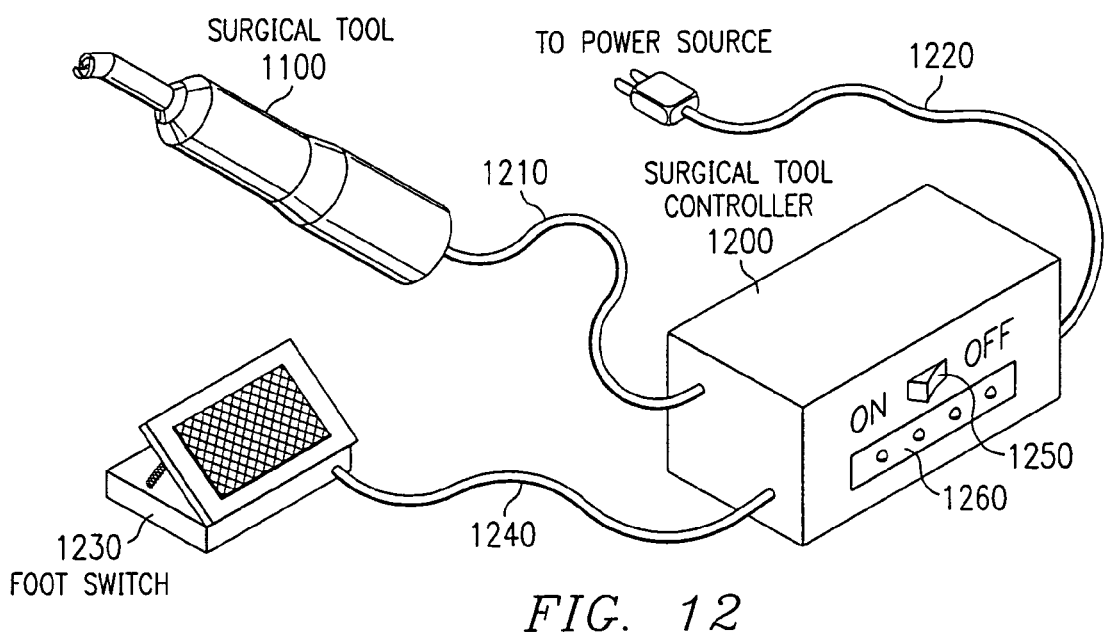
FIG. 12 shows a surgical tool controller for controlling the operation of the surgical tool of the present invention and a foot switch for activating the surgical tool.

FIG. 12 shows surgical tool 1100 and a surgical tool controller 1200 for controlling the operation of surgical tool 1100. Surgical tool 1100 is coupled to surgical tool controller 1200 through control cable 1210. Control cable 1210 provides electrical power to surgical tool 1100 under the control of surgical tool controller 1200 to power the operation of blade 1140. Control cable 1210 also provides an "earth ground" to surgical tool 1100. Surgical tool controller 1200 receives external electrical power through power cord 1220. It is also possible to use a battery (not shown) or other power source.

Foot switch 1230 is coupled to surgical tool controller 1200 through signal line 1240. When the surgeon is ready to rotate blade 1140 to make an incision in eye 100 the surgeon steps on foot switch 1230. Foot switch 1230 then sends a control signal to surgical tool controller 1200 through signal line 1240. In response, surgical tool controller 1220 activates electrical power to surgical tool 1100 to cause blade 1140 to rotate in a forward direction and make the desired incision in eye 100. In one advantageous embodiment the time required for blade 1140 to make an incision in eye 100 is approximately two (2) seconds. Other suitable time durations may be appropriate. The incision is complete after blade 1140 has reached the end of its rotation in the forward direction. Surgical tool controller 1200 then automatically causes blade 1140 to rotate back out of the incision. Surgical tool 1100 is then ready to make another incision.

If the surgeon releases his or her foot from foot switch 1230 during the time period during which the incision is being made, foot switch 1230 immediately sends a control signal to surgical tool controller 1200 through signal line 1240. In response, surgical tool controller 1220 causes the forward motion of blade 1140 to cease. If the surgeon steps on foot switch 1230 again blade 1140 resumes its rotation in the forward direction. If the surgeon desires to rotate blade 1140 out of the incision the surgeon manually presses a "blade retract" control button on surgical tool controller 1200.

Surgical tool controller 1200 comprises a switch 1250 (on/off switch 1250) for activating the operation of surgical tool controller 1200. Surgical tool controller 1200 also comprises indicator lights 1260 that indicate the operational status of surgical tool controller 1200. It is understood that other control methods may also be used to control the operation of surgical tool 1100 such as voice activated controls, hand controls, finger controls, and other biometric controls.

Figure 13:
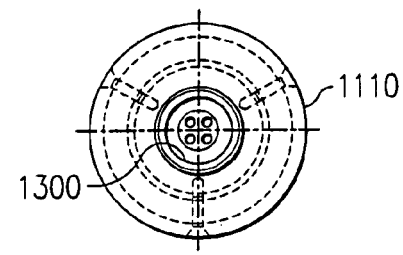
FIG. 13 shows an end view of the surgical tool of the present invention showing a control cable receptacle capable of receiving a control cable to supply electrical power to the surgical tool.

FIG. 13 shows an end view of base housing 1110 of surgical tool 1100. Base housing 1110 comprises a control cable receptacle 1300 capable of receiving control cable 1210 to electrically power surgical tool 1100. In this advantageous embodiment control cable receptacle 1300 is capable of receiving four (4) individual power plugs of control cable 1210.

Figure 14:
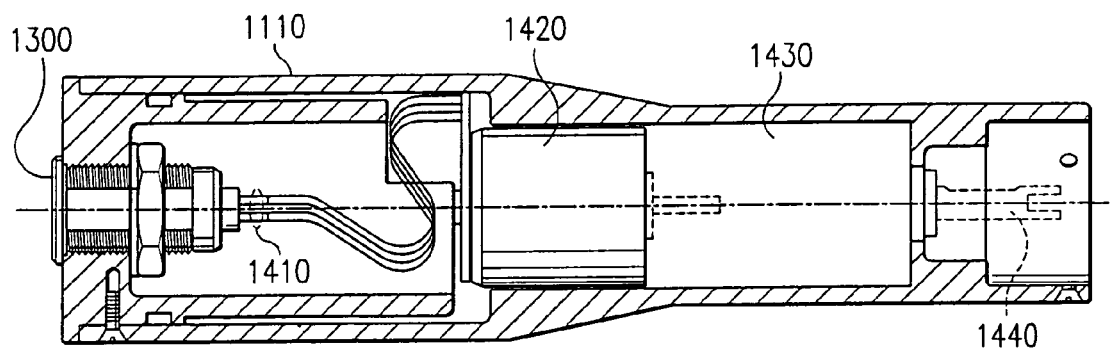
FIG. 14 shows a cross section of a first portion of the surgical tool of the present invention showing a base housing containing a control cable receptacle, a drive motor, a gearbox, and a drive shaft capable of being rotated by the drive motor.
Figure 17:
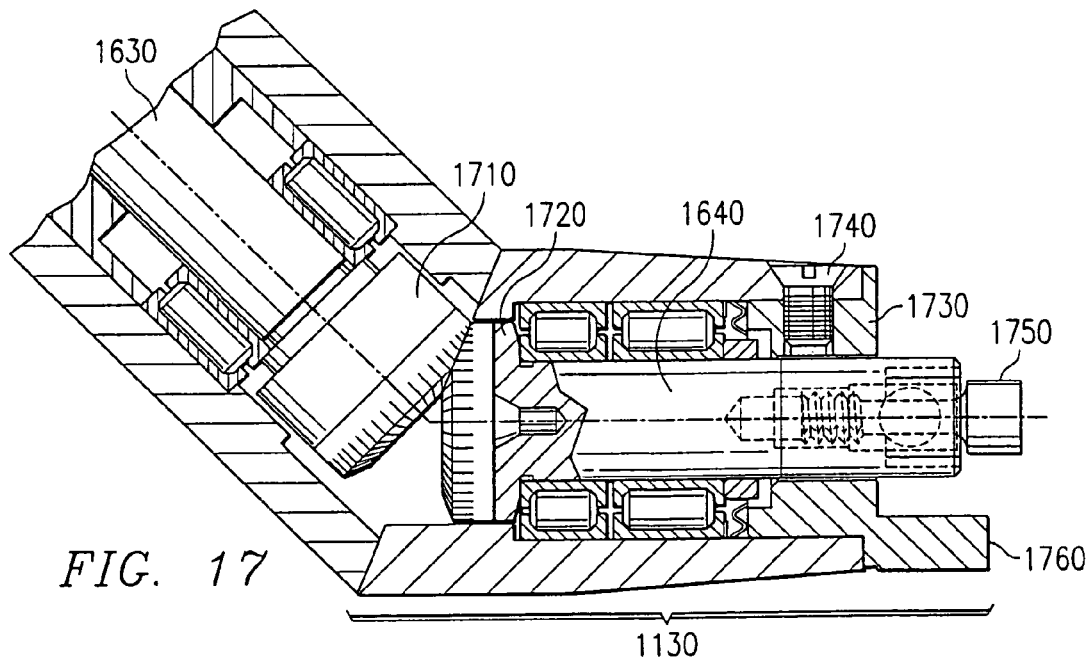
FIG. 17 shows a more detailed cross sectional view of the interconnection of the drive shaft housing and the blade mount housing shown in FIG. 16.
Figures 15, 16:
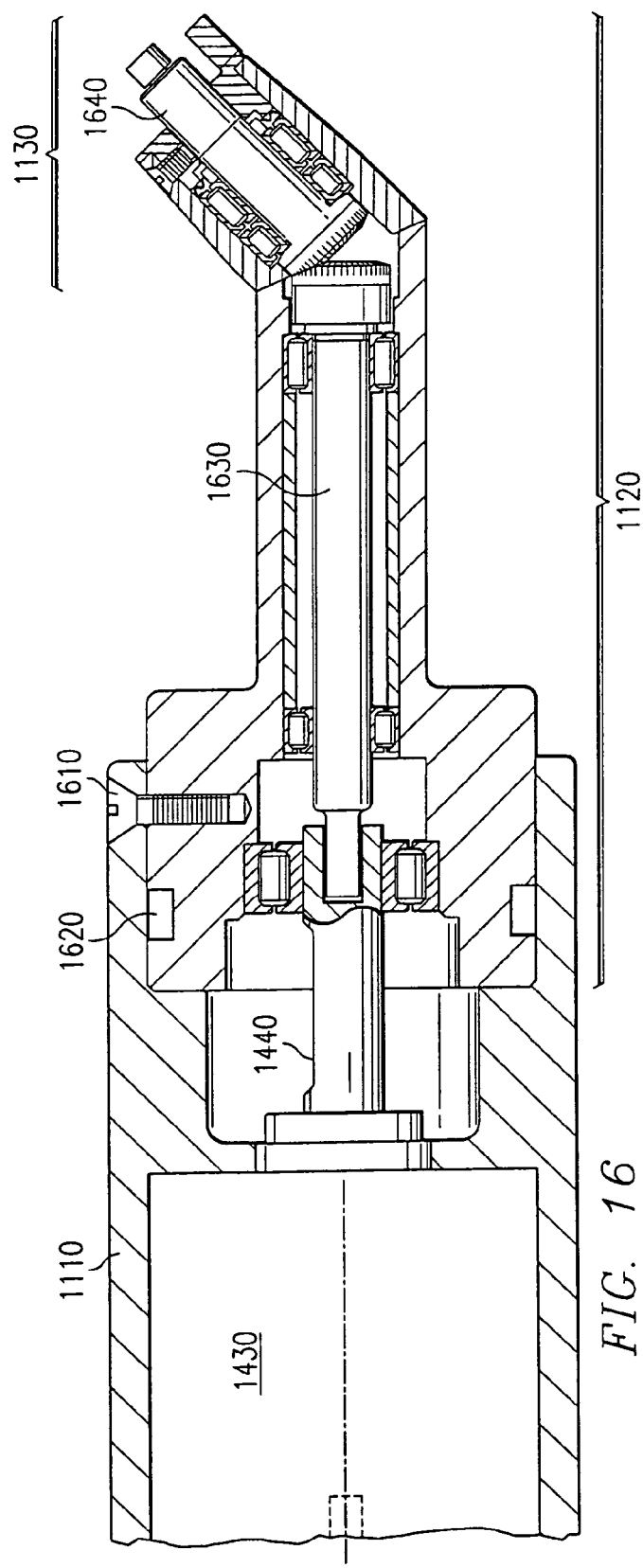
FIG. 15 shows a schematic circuit diagram illustrating how electrical power is supplied to the drive motor of the surgical tool.
FIG. 16 shows a cross section of a second portion of the surgical tool showing a drive shaft housing mounted within an end of the base housing of the surgical tool, and showing a blade mount housing mounted on the drive shaft housing an angle to a central axis of the drive shaft housing.

FIG. 14 shows a cross section of base housing 1110. Base housing 1110 comprises control cable receptacle 1300, four power lines (collectively designated 1410), drive motor 1420, gearbox 1430, and a drive shaft 1440. When control cable 1210 is placed into control cable receptacle 1300, four power plugs of control cable 1210 make contact with the four power lines 1410. As shown in FIG. 15, two of the four power lines (line 1 and line 2) are coupled to a first winding circuit (circuit A) of motor 1420. The other two of the four power lines (line 3 and line 4) are coupled to a second winding circuit (circuit B) of motor 1420.

When surgical tool controller 1200 powers up line 1 and line 2, then motor 1420 rotates in one direction (e.g., counterclockwise). When surgical tool controller 1200 powers up line 3 and line 4, then motor 1420 rotates in the other direction (e.g., clockwise). In this manner motor 1420 provides both rotational motion to rotate blade 1140 forward to make an incision in eye 100 and provides rotational motion to rotate blade 1140 backwards to remove blade 1140 from the incision made in eye 100. The two types of rotational motion will be collectively referred to as "bidirectional rotational motion."

The rotational motion generated by motor 1420 is coupled to gearbox 1430. In one advantageous embodiment gearbox 1430 reduces the rotational speed provided by motor 1420 by a factor of sixty six (66:1). That is, the rotational speed output by gearbox 1430 is one sixty sixth ($\frac{1}{66}$) of the rotational speed provided to gearbox 1430 by motor 1420. This amount of rotational speed reduction is necessary to increase the torque and because the rotational speed provided by motor 1420 is too great to be used to rotate blade 1140 directly. The rotational output from gearbox 1430 is coupled to drive shaft 1440 of base housing 1110.

FIG. 16 shows a cross sectional view of drive shaft housing 1120 mounted within base housing 1110 and a cross sectional view of blade mount housing 1130. Blade 1140 is not shown in FIG. 16. Drive shaft housing 1120 seats within a receptacle of base housing 1110 and is held in place by conventional means such as a screw 1610. O-ring 1620 seals the juncture between the receptacle of base housing 1110 and drive shaft housing 1120.

Drive shaft housing 1120 comprises drive shaft 1630. Drive shaft 1630 is supported within drive shaft housing 1120 by conventional bearings. As shown in FIG. 16, drive shaft 1630 is coupled to drive shaft 1440 of base housing 1110. The coupling of drive shaft 1630 and drive shaft 1440 is supported by conventional bearings. Drive shaft 1440 rotates drive shaft 1630.

Blade mount housing 1130 comprises drive shaft 1640. Drive shaft 1640 is supported within blade mount housing 1130 by conventional bearings. As shown in FIG. 16, drive shaft 1640 is coupled to drive shaft 1630 of drive shaft housing 1120 at an angle. As shown in greater detail in FIG. 17, a beveled gear 1710 of drive shaft 1630 engages a beveled gear 1720 of drive shaft 1640. As drive shaft 1630 is rotated, the rotational motion of beveled gear 1720 of drive shaft 1630 is imparted to beveled gear 1720 of drive shaft 1640. The rotational motion of drive shaft 1640 is used to rotate blade 1140 (not shown in FIGS. 16 and 17) mounted on blade mount housing 1130.

Base plate 1730 seats within an end of blade mount housing 1130 and is held in place by conventional means such as a screw 1740. Drive shaft 1640 extends through an aperture in base plate 1730 so that base plate 1730 also provides support for drive shaft 1640. Conventional means such as a screw 1750 may be used to secure blade 1140 to drive shaft 1640. Screw 1750 may also serve as an extension 1750 of drive shaft 1640 onto which blade 1140 may be mounted. Base plate 1730 comprises portions forming a blade guide 1760 for guiding the rotation of blade 1140 and for stopping the rotation of blade 1140 after blade 1140 has been rotated by a desired amount.

The blade 1140 of surgical tool 1100 is shown in FIGS. 18-20. FIG. 18 shows a top plan view of blade 1140. FIG. 19 shows a side view of blade 1140. FIG. 20 shows a perspective view of blade 1140. Blade 1140 comprises support arm 1810 adapted to be mounted on an end of drive shaft 1640 of blade mount housing 1130. Blade 1140 also comprises a curved cutting blade 1820 for making an incision in the sclera 102 of eye 100. In an advantageous embodiment of the invention, (1) support arm 1810 and curved cutting blade 1820 are formed as a unitary structure, and (2) curved cutting blade 1820 is circularly curved, and (3) curved cutting blade 1820 has end portions defining a tapered cutting point 1830.

When drive shaft 1640 is rotated, support arm 1810 rotates around the axis of drive shaft 1640. This causes curved cutting blade 1820 to rotate around the axis of drive shaft 1640. The dimensions of curved cutting blade 1820 are chosen so that the incision made by curved cutting blade 1820 in the sclera 102 of eye 100 has the desired dimensions to form scleral pocket 120. Scleral pocket 120 should be approximately four millimeters (4.0 mm) long, one and one half millimeters (1.5 mm) wide, and four hundred microns (400 μm) deep. Four hundred microns (400 μm) is equivalent to four-tenths of a millimeter (0.4 mm).

FIG. 21 shows an external side view of drive shaft housing 1120 and blade mount housing 1130 and blade 1140. Aperture 2110 is provided to receive screw 1610 to fasten drive shaft housing 1120 within base housing 1110. Groove 2120 is provided to receive O-ring 1620 to seal the juncture between the receptacle of base housing 1110 and drive shaft housing 1120. Aperture 2130 is provided to receive screw 1740 to fasten base plate 1730 within blade mount housing 1130.

An external reference line 2140 is marked on the surface of blade mount housing 1130. Line 2140 is located five and one half millimeters (5.5 mm) from the end of blade mount housing 1130. Line 2140 allows the surgeon to properly align blade 1140 during the surgical process. The surgeon aligns line 2140 with the limbus 106 of eye 100. This alignment properly positions blade 1140 to make an incision at the desired location on sclera 102 of eye 100.

Figure 22:
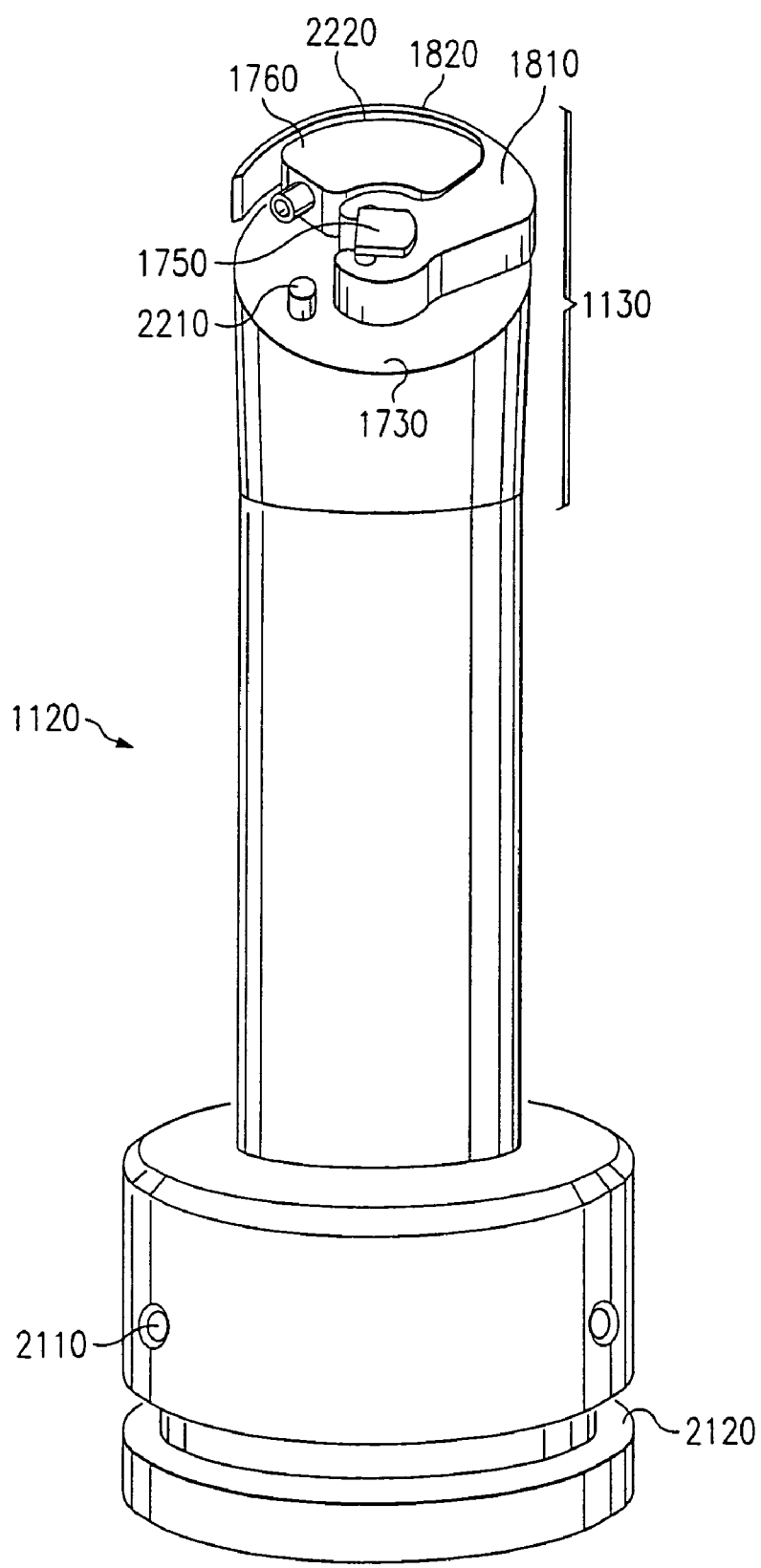
FIG. 22 shows a perspective view of the drive shaft housing and an end view of the blade mount housing of the surgical tool of the present invention.

FIG. 22 shows a perspective view of driveshaft housing 1120 and an end view of blade mount housing 1130. Base plate 1730 forms the end of blade mount housing 1130. The components of blade 1140 are shown separately as support arm 1810 and curved cutting blade 1820. Support arm 1810 is mounted on drive shaft 1640 by snapping an end of support arm 1810 onto an extension 1750 of drive shaft 1640. In an alternative embodiment, support arm 1810 may be mounted on drive shaft 1640 using conventional means such as a screw.

Support arm 1810 is shown rotated forward to a position where it has abutted an edge of blade guide 1760. In this position curved cutting blade 1820 has completed its rotation and would have completed an incision if it has been adjacent to eye 100. Blade guide 1760 also guides the rotation of blade 1140. Blade guide 1760 is formed having a circularly shaped surface 2220 that is concentric with curved cutting blade 1820. The length of support arm 1810 supports curved cutting blade 1820 at a distance that is approximately four hundred microns (400 μm) away from the circularly shaped surface 2220 of blade guide 1760.

At the start of the surgical process the surgeon places the circularly shaped surface 2220 of blade guide 1760 on the sclera 102 of eye 100. The surgeon then begins the rotation of blade 1140 by stepping on foot switch 1230. As long as the surgeon is stepping on foot switch 1230 blade 1140 continues to advance in a forward direction as support arm 1810 of blade 1140 rotates curved cutting blade 1820. Curved cutting blade 1820 then passes through sclera 102 of eye 100 at a depth of approximately four hundred microns (400 μm) to make the desired incision. The surgeon removes his or her foot from foot switch 1230 if the surgeon determines that it is desirable to stop the rotation of blade 1140. Surgical tool controller 1200 will immediately stop the rotation of blade 1140 and will then automatically rotate blade 1140 out of the incision.

The components of blade 1140 (support arm 1810 and curved cutting blade 1820) may also be rotated back to abut the safety stop 2210. Blade guide 1760 and safety stop 2210 limit the rotational range of blade 1140 to only the rotation needed to perform the desired incisions.

Figure 23:
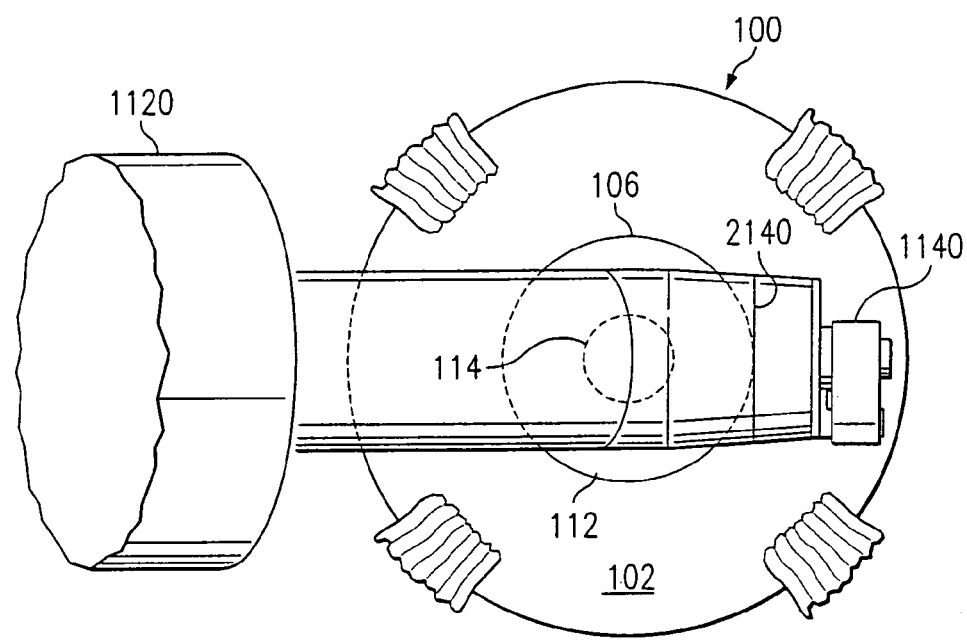
FIG. 23 shows a top view illustrating how the surgical tool of the present invention is to be positioned over an eye to make incisions in the sclera of the eye.

FIG. 23 shows a top view illustrating how surgical tool 1100 is to be positioned over eye 100 to make incisions in the sclera 102 of eye 100. Eye 100 comprises sclera 102, iris 112, pupil 114, and limbus 106 (the boundary between sclera 102 and iris 112). Iris 114 and portions of limbus 106 are shown in dotted outline in FIG. 23 because they are obscured by drive shaft housing 1120 and blade mount housing 1130. As previously mentioned, the surgeon aligns line 2140 on blade mount housing 1130 with the limbus 106 of eye 100. This alignment properly positions blade 1140 to make an incision at the desired location on sclera 102 of eye 100.

Figure 24:
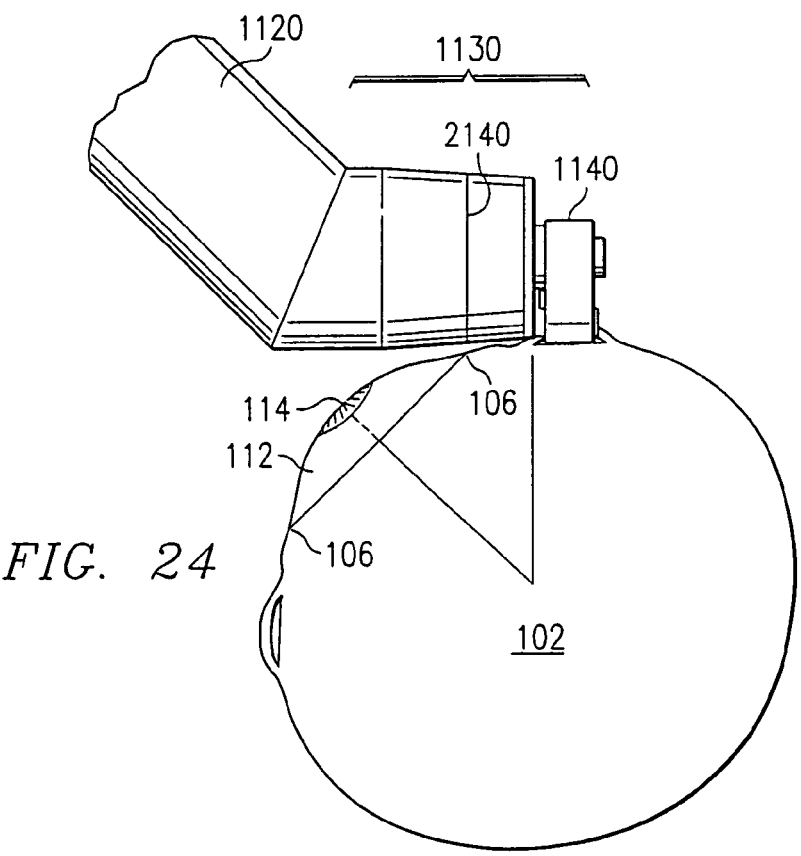
FIG. 24 shows a side view illustrating how the surgical tool of the present invention is to be positioned over an eye to make incisions in the sclera of the eye.

FIG. 24 shows a side view illustrating how surgical tool 1100 is to be positioned over eye 100 to make incisions in the sclera 102 of eye 100. The surgeon aligns line 2140 on blade mount housing 1130 with limbus 106 of eye 100. As described with reference to FIG. 23 this alignment properly positions blade 1140. The reason for mounting blade mount housing 1130 at an angle with respect to the central axis of drive shaft housing 1120 is now apparent. It is to facilitate the placement of blade mount housing 1130 on eye 100 during the surgical process.

Figure 25:
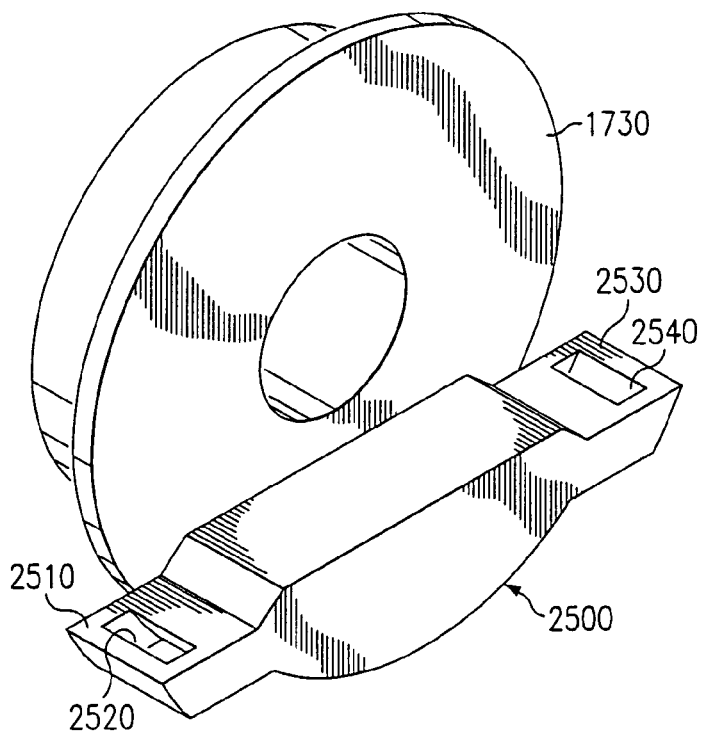
FIG. 25 shows a perspective view of an alternate advantageous embodiment of a blade guide of the surgical tool of the present invention to guide the motion of a blade when the blade is rotated to make incisions in the sclera of an eye.

FIG. 25 shows a perspective view of an alternate advantageous embodiment 2500 of blade guide 1760. Blade guide 2500 is mounted on base plate 1730. In this embodiment blade guide 2500 comprises an end portion 2510 forming a first blade slot 2520 on a first end of blade guide 2500. Blade guide 2500 also comprises an end portion 2530 forming a second blade slot 2540 on a second end of blade guide 2500. Blade guide 2500 operates in the same manner as blade guide 1760 except that the end portions, 2510 and 2530, of blade guide 2500 provide additional external protection for curved cutting blade 1820 of blade 1140. End portions, 2510 and 2530, may also be seated against sclera 102 of eye 100 during the surgical process to provide additional peripheral contact between blade guide 2500 and sclera 102 and to ensure a proper length for an incision.

Figure 26:
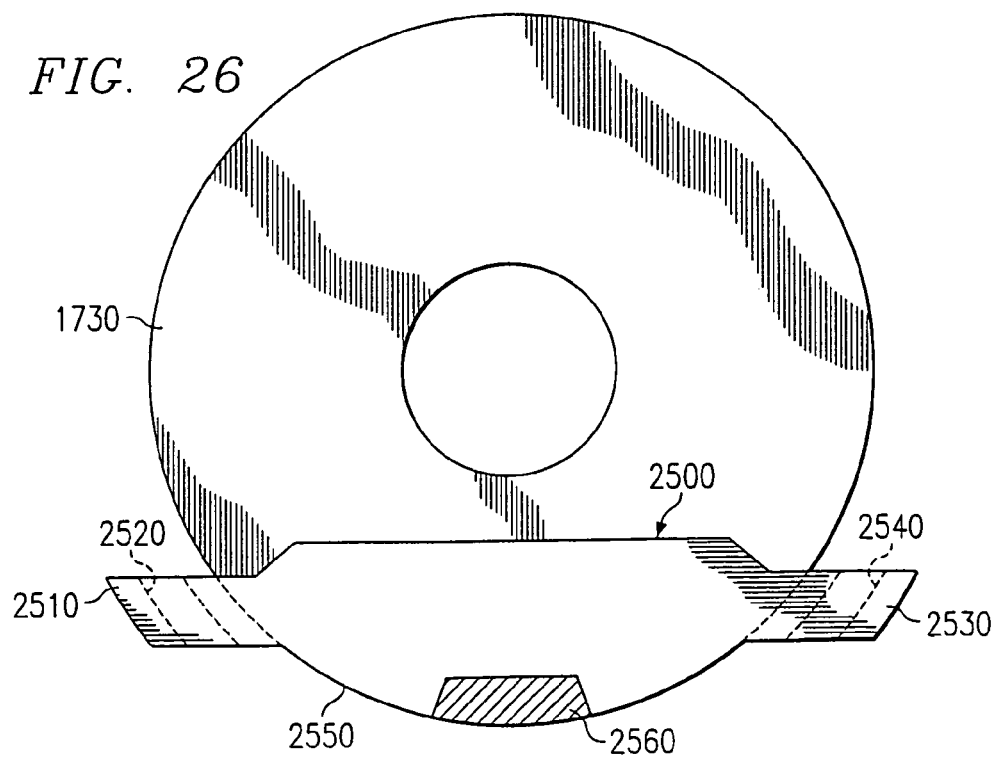
FIG. 26 shows an end view of the blade guide shown in FIG. 25.

FIG. 26 shows an end view of blade guide 2500. Blade guide 2500 is formed having a circularly shaped surface 2550 that is concentric with curved cutting blade 1820. The length of support arm 1810 supports curved cutting blade 1820 at a distance that is approximately four hundred microns (400 μm) away from the circularly shaped surface 2550 of blade guide 2500.

At the start of the surgical process the surgeon places circularly shaped surface 2550 of blade guide 2500 on the sclera 102 of eye 100. A pressure sensor 2560 within blade guide 2500 senses the pressure of the sclera 102 against the circularly shaped surface 2550 of blade guide 2500. A pressure sensor control line (not shown) connects pressure sensor 2560 to surgical tool controller 1200. Pressure sensor 2560 senses whether there is sufficient pressure between the surface of sclera 102 and the circularly shaped surface 2550 of blade guide 2500. If there is not sufficient pressure then any incision made by blade 1140 would be too shallow. If pressure sensor 2560 does not detect sufficient pressure then surgical tool controller 1200 will not allow blade 1140 of surgical tool 1100 to rotate. If pressure sensor 2560 does detect sufficient pressure then surgical tool controller 1200 will allow blade 1140 of surgical tool 1100 to rotate.

The surgeon begins the rotation of blade 1140 by stepping on foot switch 1230. As long as the surgeon is stepping on foot switch 1230 blade 1140 continues to advance in a forward direction as support arm 1810 of blade 1140 rotates curved cutting blade 1820. Curved cutting blade 1820 then passes through sclera 102 of eye 100 at a depth of approximately four hundred microns (400 μm) to make the desired incision. The surgeon removes his or her foot from foot switch 1230 if the surgeon determines that it is desirable to stop the rotation of blade 1140. Surgical tool controller 1200 will immediately cause the forward motion of blade 1140 to cease. If the surgeon steps on foot switch 1230 again blade 1140 resumes its rotation in the forward direction. If the surgeon desires to rotate blade 1140 out of the incision the surgeon manually presses a "blade retract" control button on surgical tool controller 1200.

Figure 27:
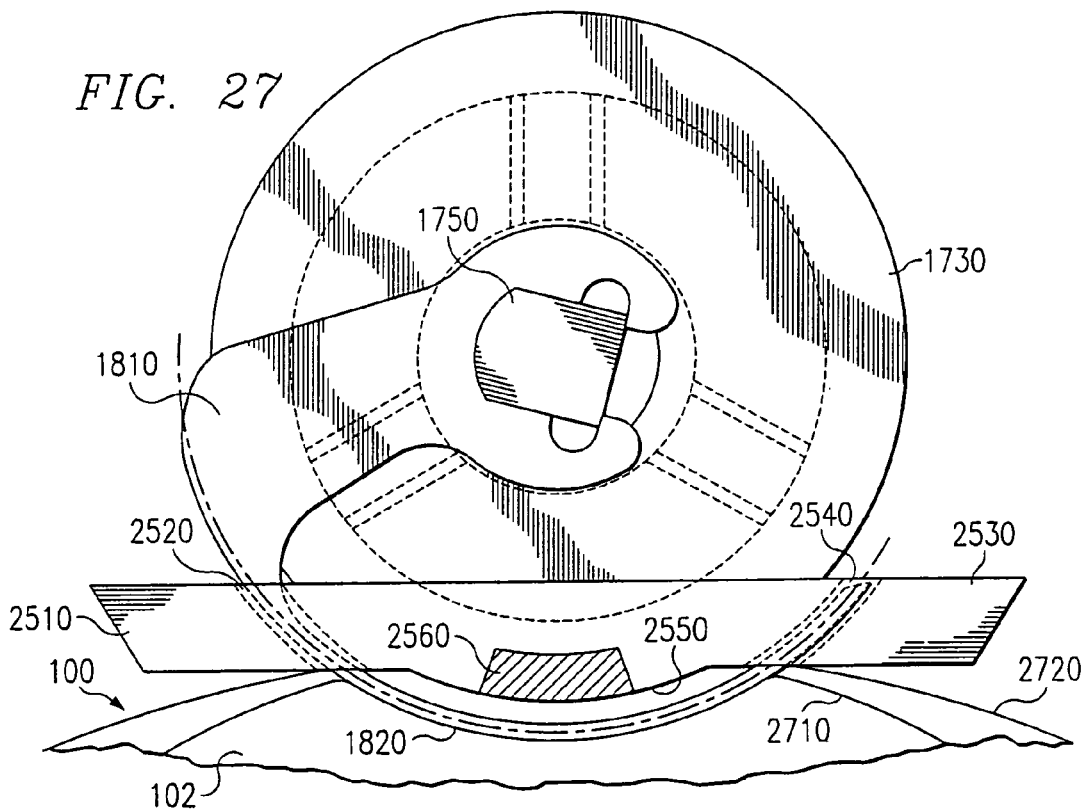
FIG. 27 shows an end view of the blade mount housing and blade guide and blade placed in contact with an eye showing how a blade passes through the blade guide when the blade is rotated to make incisions in the sclera of an eye.

FIG. 27 shows an end view of blade guide 2500 showing how curved cutting blade 1820 passes through first blade slot 2520 of blade guide 2500, and through sclera 102 of eye 100, and through second blade slot 2540 of blade guide 2500 when support arm 1810 of blade 1140 is rotated. Curve 2710 represents the surface contour of sclera 102 of eye 100 before blade guide 2500 is placed in contact with eye 100. Curve 2720 represents the surface contour of eye 100 after blade guide 2500 is placed in contact with sclera 102 of eye 100. Pressure applied to keep blade guide 2500 in contact with sclera 102 of eye 100 temporarily makes the surface contour of the sclera 102 of eye 100 concave during the incision process.

As can be seen in FIG. 27, the curved cutting blade 1820 passes through the anterior surface of the sclera 102 without passing through the posterior surface of the sclera 102.

Figure 28:
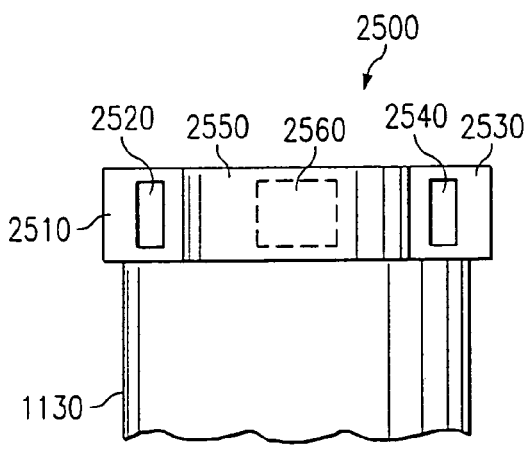
FIG. 28 shows a side view of an end portion of the blade mount housing showing a portion of the blade guide that is placed in contact with an eye during the process of making incisions in the sclera of the eye.

FIG. 28 shows a side view of an end portion of blade mount housing 1130 showing the surface 2550 of blade guide 2500 that is placed in contact with sclera 102 of eye 100. Pressure sensor 2560 in blade guide 2500 is shown in dotted outline. In this view curved cutting blade 1820 of blade 1140 is retracted. First blade slot 2520 and second blade slot 2540 of blade guide 2500 are visible.

Figure 29:
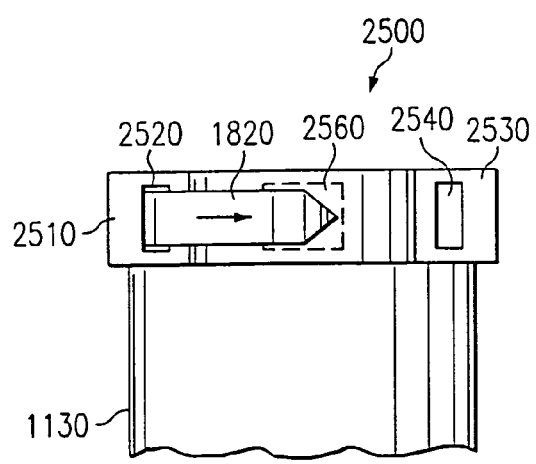
FIG. 29 shows how a blade moves through the blade guide shown in FIG. 28 during the process of making incisions in the sclera of the eye.

FIG. 29 also shows a side view of an end portion of blade mount housing 1130 showing the surface 2550 of blade guide 2500 that is placed in contact with sclera 102 of eye 100. As before, pressure sensor 2560 in blade guide 2500 is shown in dotted outline. In this view curved cutting blade 1820 of blade 1140 has begun to be rotated through first blade slot 2520. Curved cutting blade 1820 is the process of rotating across surface 2550 of blade guide 2500 and is proceeding toward second blade slot 2540 of blade guide 2500. FIG. 29 shows how curved cutting blade 1820 moves through blade guide 2500 during the process of making incisions in sclera 102 of eye 100.

The counterclockwise motion of the curved cutting blade 1820 hitting the surface of the sclera 102 of eye 100 tends to push surgical tool 1100 in the opposite direction causing surgical tool 1100 to translate opposite to the tangent force generated by curved cutting blade 1820. It is therefore necessary to firmly hold the surface of the sclera 102 against the surgical tool 1100 during the process of making the incision.

Figure 30:
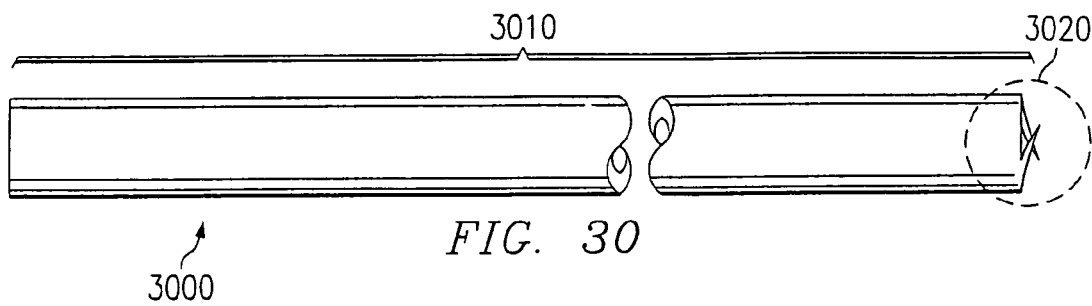
FIG. 30 shows and exemplary scleral tissue fixation tool of the present invention.

In one advantageous embodiment of the invention, a scleral tissue fixation tool 3000 is utilized to restrain the movement of surgical tool 1100. As shown in FIG. 30, scleral tissue fixation tool 3000 generally comprises a shaft 3010 having a fixation end 3020 that is capable of engaging and holding a portion of the surface of sclera 102. Scleral tissue fixation tool 3000 applies a force opposite to the tangent force generated by the curved cutting blade 1820 coming in contact with the sclera 102. The shaft 3010 is manually held and operated by the surgeon during the process of making an incision so that surgical tool 1100 does not move.

Figure 31:
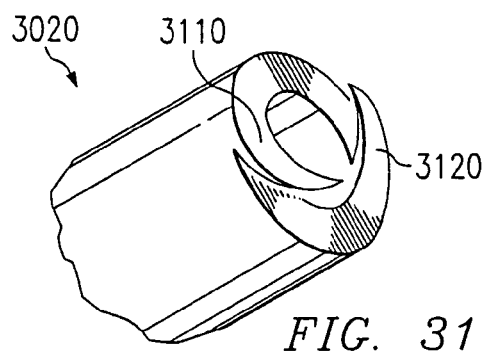
FIG. 31 shows a perspective view of an advantageous embodiment of a fixation end of a scleral tissue fixation tool of the present invention.

In one advantageous embodiment, scleral tissue fixation tool 3000 is approximately fifteen centimeters (15.0 cm) to twenty centimeters (20.0 cm) long and approximately one and one half millimeters (1.5 mm) wide. FIG. 31 shows a perspective view of fixation end 3020 of scleral tissue fixation tool 3000. Fixation end 3020 comprises a first fixation barb 3110 formed on a first side of the end of shaft 3010. First fixation barb 3110 is formed by slicing and lifting up an end portion of shaft 3010. The amount of separation of first fixation barb 3110 from the end of shaft 3010 is in the range from three tenths of a millimeter (0.30 mm) to four tenths of a millimeter (0.40 mm).

Fixation end 3020 also comprises a second fixation barb 3120 formed on a second side of the end of shaft 3010. Second fixation barb 3120 is formed by slicing and lifting up an end portion of shaft 3010. The amount of separation of second fixation barb 3120 from the end of shaft 3010 is the same as the amount of separation of first fixation barb 3110.

To restrain the translational movement of surgical tool 1100 the surgeon uses scleral tissue fixation tool 3000 to engage and hold a portion of sclera 102 near the first blade slot 2520 of blade guide 2500. First blade slot 2520 is where curved cutting blade 1820 first impacts sclera 102 and tends to cause translation of surgical tool 1100. The surgeon places the fixation end 3020 of the scleral tissue fixation tool 3000 onto the sclera 102 and twists shaft 3010 to the right to engage first fixation barb 3110 and second fixation barb 3120 into sclera 102. The surgeon holds the shaft 3010 against surgical tool 1100 during the incision process. After the incision has been made the surgeon releases the scleral tissue fixation tool 3000 from sclera 102 by twisting shaft 3010 to the left to disengage the grip of fixation barbs, 3110 and 3120.

The scleral tissue fixation tool 3000 shown in FIG. 31 is a "right twist" tool. It engages by twisting shaft 3010 to the right and disengages by twisting shaft 3010 to the left.

Figure 32:
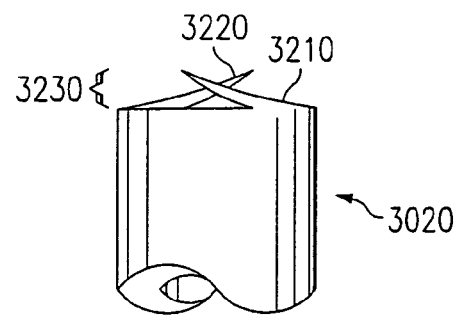
FIG. 32 shows a side view of an alternate advantageous embodiment of a fixation end of a scleral tissue fixation tool of the present invention.

FIG. 32 shows an alternative advantageous embodiment of scleral tissue fixation tool 3000. The scleral tissue fixation tool 3000 shown in FIG. 32 is a "left twist" tool. It engages by twisting shaft 3010 to the left and disengages by twisting shaft 3010 to the right. Otherwise, the scleral tissue fixation tool 3000 shown in FIG. 32 is identical to the scleral tissue fixation tool 3000 shown in FIG. 31. It comprises a first fixation barb 3210 and a second fixation barb 3220. The amount of separation 3230 of first fixation barb 3210 from the end of shaft 3010 is in the range from three tenths of a millimeter (0.30 mm) to four tenths of a millimeter (0.40 mm). The amount of separation of second fixation barb 3220 from the end of shaft 3010 is the same as the amount of separation of first fixation barb 3210.

In an alternate advantageous embodiment of the invention, a special type of vacuum operated blade guide 3300 is utilized to restrain the movement of the sclera 102 and the translational movement of surgical tool 1100 generated from the impact of the curved cutting blade 1820. As will be more fully described, a vacuum is applied to seat blade guide 330 against sclera 102 during the process of making an incision.

Figure 33:
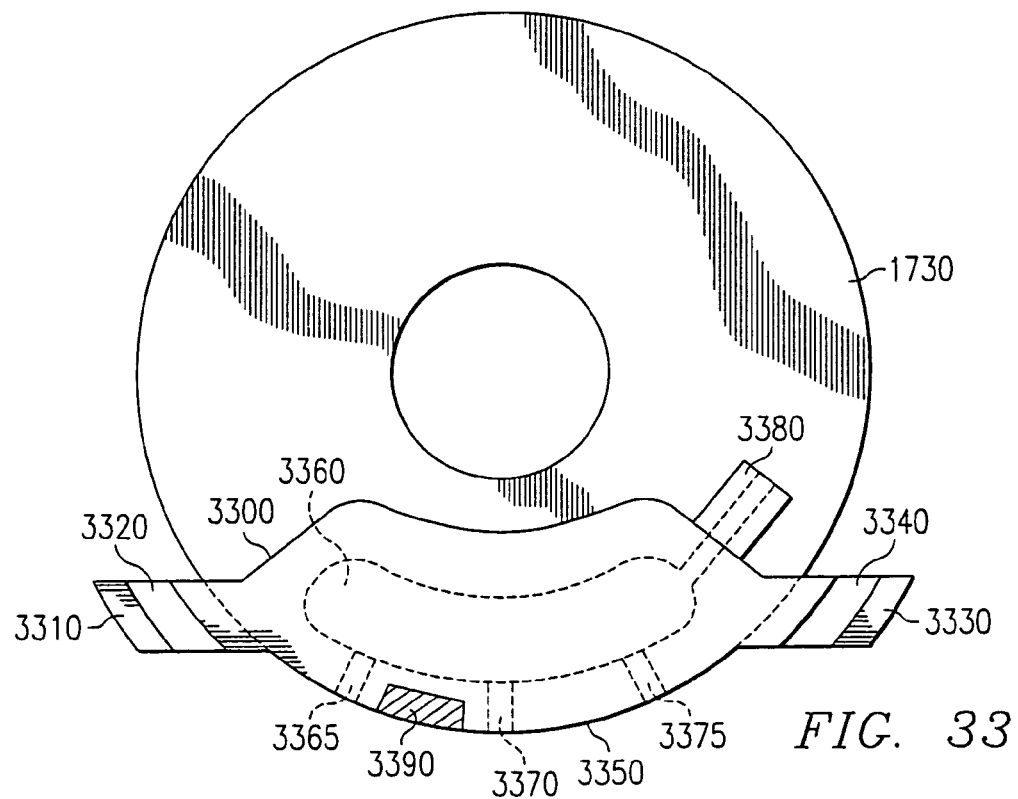
FIG. 33 shows a side view of an alternative advantageous embodiment of a blade guide of the surgical tool of the present invention comprising an interior vacuum chamber.

FIG. 33 shows an end view of blade guide 3300. Blade guide 3300 is mounted on base plate 1730. In this embodiment blade guide 3300 comprises an end portion 3310 forming a first blade slot 3320 on a first end of blade guide 3300. Blade guide 3300 also comprises an end portion 3330 forming a second blade slot 3340 on a second end of blade guide 3300. The end portions, 3310 and 3330, of blade guide 3300 provide additional external protection for curved cutting blade 1820 of blade 1140. End portions, 3310 and 3330, are seated against sclera 102 of eye 100 during the surgical process to provide additional peripheral contact between blade guide 3300 and sclera 102 to ensure proper scleral pocket length.

Blade guide 3300 is formed having a circularly shaped surface 3350 that is concentric with curved cutting blade 1820. The length of support arm 1810 supports curved cutting blade 1820 at a distance that is approximately four hundred microns (400 μm) away from the circularly shaped surface 3350 of blade guide 3300.

At the start of the surgical process the surgeon places circularly shaped surface 3350 of blade guide 3300 on the sclera 102 of eye 100. A pressure sensor 3390 within blade guide 3300 senses the pressure of the sclera 102 against the circularly shaped surface 3350 of blade guide 3300. A pressure sensor control line (not shown) connects pressure sensor 3390 to surgical tool controller 1200. Pressure sensor 3390 senses whether there is sufficient pressure between the surface of sclera 102 and the circularly shaped surface 3350 of blade guide 3300. If there is not sufficient pressure then any incision made by blade 1140 would be too shallow. If pressure sensor 3390 does not detect sufficient pressure then surgical tool controller 1200 will not allow blade 1140 of surgical tool 1100 to rotate. If pressure sensor 3390 does detect sufficient pressure then surgical tool controller 1200 will allow blade 1140 of surgical tool 1100 to rotate.

The surgeon begins the rotation of blade 1140 by stepping on foot switch 1230. As long as the surgeon is stepping on foot switch 1230 blade 1140 continues to advance in a forward direction as support arm 1810 of blade 1140 rotates curved cutting blade 1820. Curved cutting blade 1820 then passes through sclera 102 of eye 100 at a depth of approximately four hundred microns (400 μm) to make the desired incision. The surgeon removes his or her foot from foot switch 1230 if the surgeon determines that it is desirable to stop the rotation of blade 1140. Surgical tool controller 1200 will immediately cause the forward motion of blade 1140 to cease. If the surgeon steps on foot switch 1230 again blade 1140 resumes its rotation in the forward direction. If the surgeon desires to rotate blade 1140 out of the incision the surgeon manually presses a "blade retract" control button on surgical tool controller 1200.

Blade guide 3300 also comprises portions that form a vacuum chamber 3360 within the interior of blade guide 3300. Blade guide 3300 also comprises portions that form a plurality of access ports, 3365, 3370, and 3375, that extend from vacuum chamber 3360 through the circularly shaped surface 3350 of blade guide 3300 to apply vacuum to the surface of sclera 102. Blade guide 3300 also comprises a vacuum coupling 3380 capable of being connected to a vacuum supply line (not shown in FIG. 33).

FIG. 34 shows a perspective view of blade guide 3300 showing end portion 3310 and first blade slot 3320. FIG. 34 also shows end portion 3330 and second blade slot 3340. Vacuum coupling 3380 extends from the exterior of blade guide 3300 to vacuum chamber 3360 (not shown in FIG. 34) located within blade guide 3300.

FIG. 35 shows an end view of blade guide 3300 showing the placement of circularly shaped surface 3350 of blade guide 3300 on the surface of sclera 102. For clarity end portion 3310, first blade slot 3320, end portion 3330 and second blade slot 3340 previously shown in FIG. 34 have been omitted from FIG. 35.

As can be seen in FIG. 35, the curved cutting blade 1820 again passes through the anterior surface of the sclera 102 without passing through the posterior surface of the sclera 102.

Vacuum coupling 3380 is coupled to a vacuum supply line 3500. Vacuum supply line 3500 provides a vacuum to vacuum chamber 3360. The vacuum causes air to pass through access ports 3365, 3370, and 3375 into vacuum chamber 3360 (shown by arrows in FIG. 35) when access ports 3365, 3370, and 3375 are open to the atmosphere. When circularly shaped surface 3350 of blade guide 3300 is placed in contact with the surface of sclera 102 the vacuum in vacuum chamber 3360 causes sclera 102 to adhere to the surface of circularly shaped surface 3350. The adhesion caused by the vacuum in vacuum chamber 3360 restrains the movement of sclera 102 when curved cutting blade 1820 is rotated into sclera 102 to make an incision.

Figure 36:
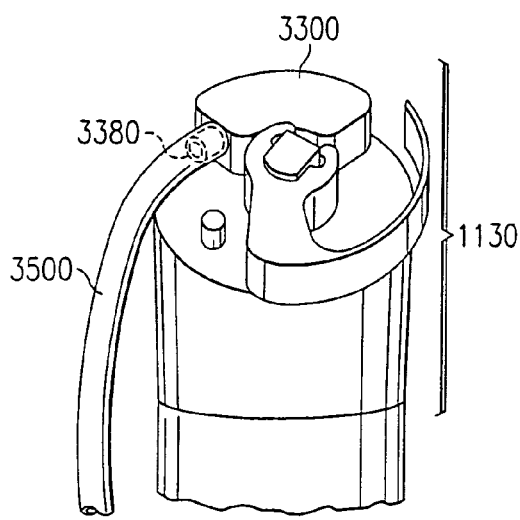
FIG. 36 shows a perspective view of a vacuum supply line coupled to the vacuum chamber blade guide of the present invention.
Figure 37:
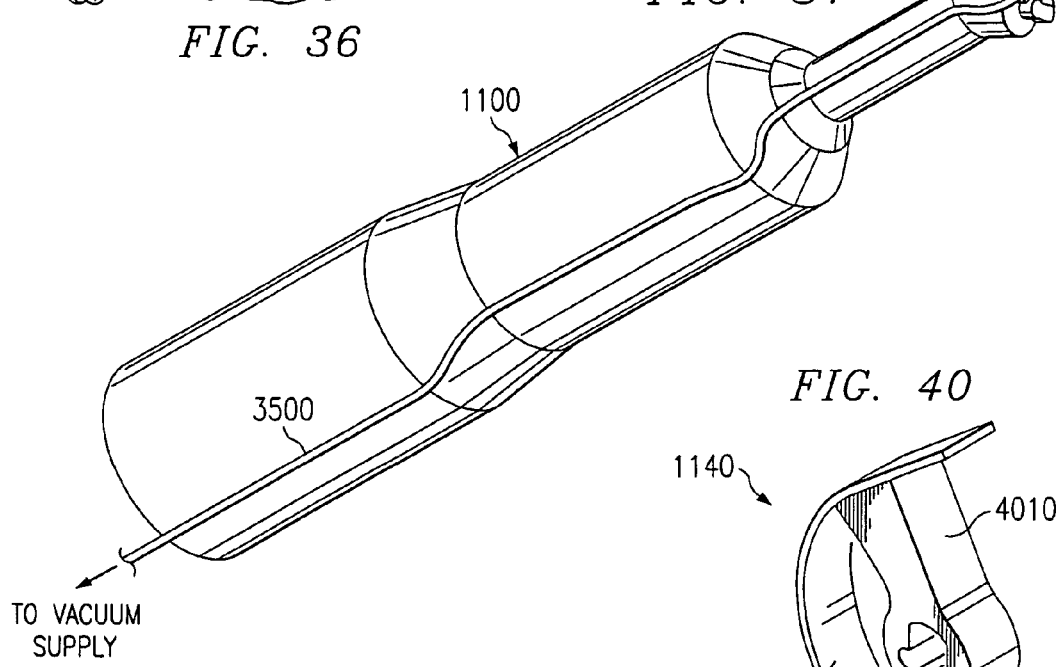
FIG. 37 shows a perspective view of the surgical tool of the present invention showing the placement of a vacuum supply line along the surgical tool.

This alternate advantageous embodiment of the present invention requires vacuum supply line 3500 be to connected to a vacuum supply (not shown). FIG. 36 shows how vacuum supply line 3500 is connected to vacuum coupling 3380 of blade guide 3300. FIG. 37 shows how vacuum supply line 3500 may be externally located along the length of surgical tool 1100.

FIG. 38 shows a flow chart of an advantageous embodiment of a method of the present invention for making incisions to form a scleral pocket 120 for a scleral prosthesis 200. The steps of the method are generally denoted with reference numeral 3800. Blade mount housing 1130 of surgical tool 1100 is positioned over sclera 102 of eye 100 by aligning external reference line 2140 of blade mount housing 1130 with limbus 106 of eye 100 (step 3810). Then blade mount housing 1130 and blade 1140 are placed into contact with sclera 102 (step 3820).

The movement of sclera 102 and surgical tool 1100 is then restrained by engaging and holding sclera 102 with scleral tissue fixation tool 3000 (step 3830). Surgical tool 1100 rotates curved cutting blade 1820 through sclera 102 to make an incision to form scleral pocket 120 (step 3840). When the incision is complete surgical tool 110 rotates curved cutting blade 1820 back out of the incision made through sclera 102 (step 3850). Then sclera 102 is released by disengaging scleral tissue fixation tool 3000 (step 3860). The incision forms scleral pocket 120 to receive scleral prosthesis 200.

FIG. 39 shows a flow chart of an alternate advantageous embodiment of a method of the present invention for making incisions to form a scleral pocket 120 for a scleral prosthesis 200. The steps of the method are generally denoted with reference numeral 3900. Blade mount housing 1130 of surgical tool 1100 is positioned over sclera 102 of eye 100 by aligning external reference line 2140 of blade mount housing 1130 with limbus 106 of eye 100 (step 3910). Then blade mount housing 1130 and blade 1140 are placed into contact with sclera 102 (step 3920).

The movement of sclera 102 and surgical tool 1100 is then restrained by engaging and holding sclera 102 with a vacuum from vacuum chamber 3360 of blade guide 33000 (step 3930). Surgical tool 1100 rotates curved cutting blade 1820 through sclera 102 to make an incision to form scleral pocket 120 (step 3940). When the incision is complete surgical tool 110 rotates curved cutting blade 1820 back out of the incision made through sclera 102 (step 3950). Then sclera 102 is released by venting the vacuum in vacuum chamber 3360 of blade guide 3300 (step 3960). The incision forms scleral pocket 120 to receive scleral prosthesis 200.

Figure 40:
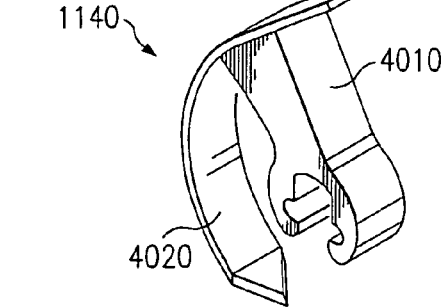
FIG. 40 shows a first perspective view of an alternate advantageous embodiment of a blade of the surgical tool of the present invention.

FIG. 40 shows a first perspective view of an alternate advantageous embodiment of blade 1140 of surgical tool 1100 of the present invention comprising support arm 4010 and curved cutting blade 4020. In the embodiment of blade 1140 shown in FIGS. 18-20 support arm 1810 and curved cutting blade 1820 are formed as a unitary structure. In the embodiment of blade 1140 shown in FIG. 40 curved cutting blade 4020 is detachable from support arm 4010.

Figure 41:
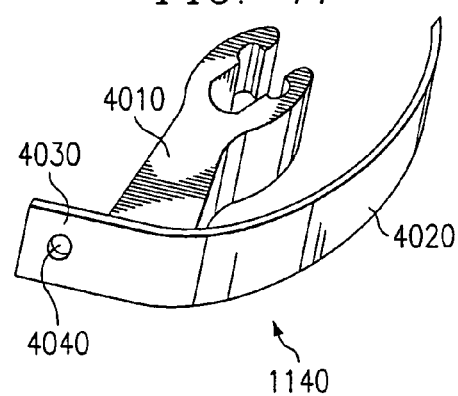
FIG. 41 shows a second perspective view of an alternate advantageous embodiment of a blade of the surgical tool of the present invention.
Figure 42:
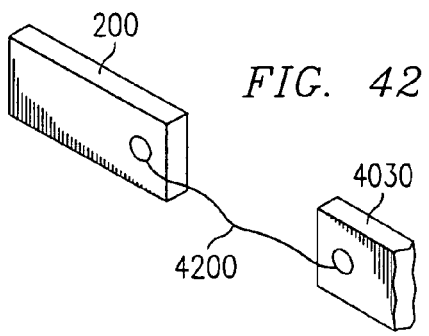
FIG. 42 shows how a scleral prosthesis may be tied to an extension of an alternate advantageous embodiment of a blade of the surgical tool of the present invention.

FIG. 41 shows a second perspective view of the alternate advantageous embodiment of blade 1140 shown in FIG. 40. Curved cutting blade 4020 comprises an extension 4030 having portions that form an aperture 4040 through extension 4030. As shown in FIG. 42, a string-like connector 4200 (e.g., a plastic fiber 4200) may be used to tie a scleral prosthesis 200 to extension 4030. Surgical tool 1100 rotates support arm 4010 and causes curved cutting blade 4020 to pass through sclera 102 as previously described.

However, in this advantageous embodiment of the invention curved cutting blade 4020 is disconnected from support arm 4010 after the incision in sclera 102 has been made. Curved cutting blade 4020 remains within the incision. Surgical tool 1100 is removed. Then the leading edge of curved cutting blade 4020 is withdrawn from the incision in the forward direction. Because curved cutting blade 4020 is tied to scleral prosthesis 200 by string-like connector 4200 the withdrawal of curved cutting blade 4020 from the incision pulls scleral prosthesis 200 into the incision. Curved cutting blade 4020 acts as a needle pulling the string-like connector 4200. Curved cutting blade 4020 is then re-attached to support arm 4010 for use in making the next incision of sclera 102.

Figure 43:
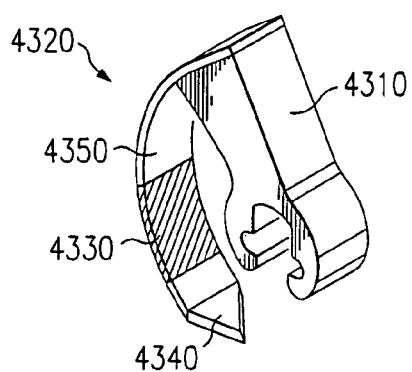
FIG. 43 shows a first perspective view of a second alternate advantageous embodiment of a blade of the surgical tool of the present invention.

FIG. 43 shows a first perspective view of a second alternate advantageous embodiment of blade 1140 of surgical tool 1100 of the present invention comprising support arm 4310 and curved cutting blade 4320. In the embodiment of blade 1140 shown in FIGS. 18-20 support arm 1810 and curved cutting blade 1820 are formed as a unitary structure. In the embodiment of blade 1140 shown in FIG. 43 curved cutting blade 4320 is detachable from support arm 4310.

Figure 44:
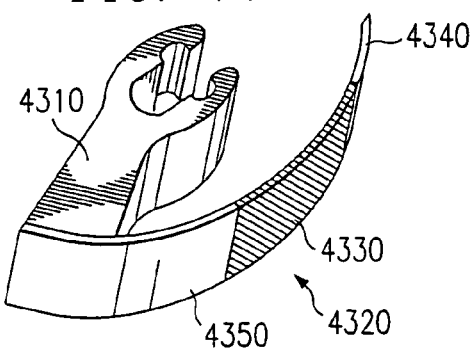
FIG. 44 shows a second perspective view of a second alternate advantageous embodiment of a blade of the surgical tool of the present invention.

In addition a central portion 4330 of curved cutting blade 4320 is detachable from the other portions of curved cutting blade 4320. Curved cutting blade 4320 comprises three portions. The three portions are (1) detachable central portion 4330, and (2) detachable tip 4340, and (3) blade portion 4350. FIG. 44 shows a second perspective view of the second alternate advantageous embodiment of blade 1140 shown in FIG. 43. Central portion 4330 is shown shaded in FIGS. 43 and 44.

Figure 45:
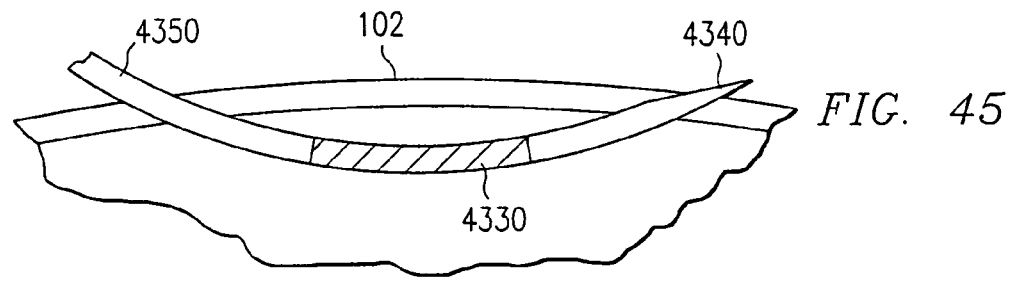
FIG. 45 shows a side view of three portions of a curved cutting blade of the second alternate advantageous embodiment of a blade of the surgical tool of the present invention.

Curved cutting blade 4320 is rotated into sclera 102 to form an incision in the manner previously described. The curved cutting blade 4320 is detached from support arm 4310 while curved cutting blade 4320 remains within the incision. FIG. 45 shows a side view of the three portions (4330, 4340, 4350) of curved cutting blade 4320 within an incision.

Then detachable tip 4340 is detached from detachable central portion 4330 (e.g., by forceps) and is removed from the incision. Then blade portion 4350 is detached from detachable central portion 4330 and is removed from the incision. Detachable central portion 4330 is left within the incision to serve as a scleral prosthesis 200.

Figure 46:
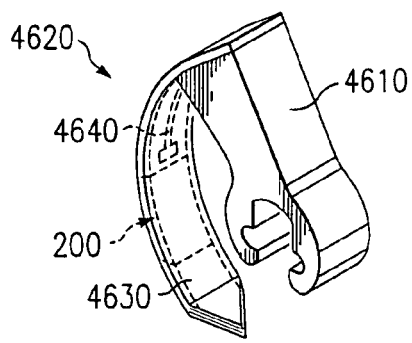
FIG. 46 shows a first perspective view of a third alternate advantageous embodiment of a blade of the surgical tool of the present invention.

FIG. 46 shows a first perspective view of a third alternate advantageous embodiment of blade 1140 of surgical tool 1100 of the present invention comprising support arm 4610 and curved cutting blade 4620. In the embodiment of blade 1140 shown in FIGS. 18-20 support arm 1810 and curved cutting blade 1820 are formed as a unitary structure. In the embodiment of blade 1140 shown in FIG. 46 curved cutting blade 4620 is detachable from support arm 4610.

Figure 47:
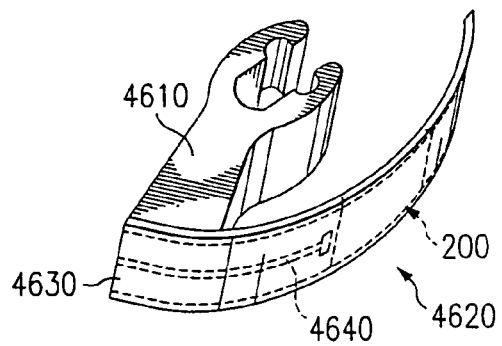
FIG. 47 shows a second perspective view of a third alternate advantageous embodiment of a blade of the surgical tool of the present invention.

In addition curved cutting blade 4620 has portions that define a conduit 4630 through curved cutting blade 4620. Slidably disposed within conduit 4630 is scleral prosthesis 200. Plunger 4640 is also slidably disposed within conduit 4630. Plunger 4630 abuts scleral prosthesis 200. FIG. 47 shows a second perspective view of the third alternate advantageous embodiment of blade 1140 shown in FIG. 46. Scleral prosthesis 200 is shown shaded in FIGS. 46 and 47.

Figure 48:
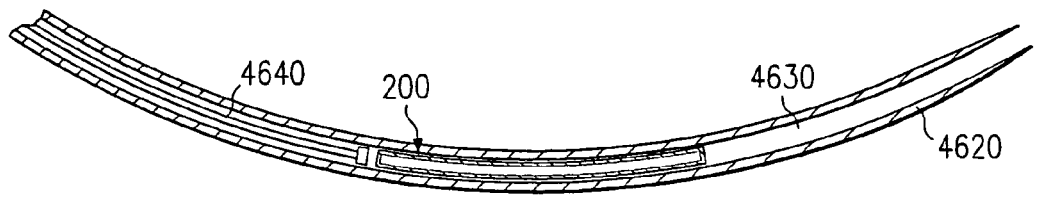
FIG. 48 shows a cross sectional side view of a curved cutting blade of the third alternate advantageous embodiment of a blade of the surgical tool of the present invention.

Curved cutting blade 4620 is rotated into sclera 102 to form an incision in the manner previously described. The curved cutting blade 4620 is detached from support arm 4610 while curved cutting blade 4620 remains within the incision. FIG. 48 shows a cross sectional side view of curved cutting blade 4620. Curved cutting blade 4620 is withdrawn from the incision. Plunger 4640 remains in place against scleral prosthesis 200 as curved cutting blade 4620 is withdrawn from the incision. Plunger 4640 prevents scleral prosthesis 200 from being withdrawn from the incision. Plunger 4640 finally pushes scleral prosthesis 200 out of conduit 4630 and into the incision. Then plunger 4640 is withdrawn from the incision leaving scleral prosthesis 200 properly placed within the incision.

In one advantageous embodiment, scleral prosthesis 200 is capable of being filled with a fluid. Scleral prosthesis 200 is filled with a fluid after scleral prosthesis 200 has been placed within the incision in order to increase the size of scleral prosthesis 200.

The invention having now-been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

What is claimed is:

1. A surgical blade, comprising:
   a support arm having a first end configured to be coupled to a surgical tool and a second end;
   a curved cutting blade that arcs around the first end of the support arm, the curved cutting blade having a substantially flat cross-section across its width and a curved cross-section along its length, the curved cutting blade having a first end coupled to the second end of the support arm, the curved cutting blade also having a second end configured to be moved through an anterior surface of scleral tissue of an eye without passing through a posterior surface of the scleral tissue of the eye to make an incision, the incision having a form of a scleral pocket that is capable of receiving a scleral eye implant prosthesis; and
   a blade guide;
   wherein the support arm is configured to rotate the second end of the curved cutting blade through a first opening and a second opening of the blade guide during a single partial revolution of the curved cutting blade such that the second end of the curved cutting blade passes through the first opening of the blade guide before entering the scleral tissue of the eye and passes through the second opening of the blade guide after exiting the scleral tissue of the eye.

2. The surgical blade of claim 1, wherein the support arm is detachably coupled to the cutting blade and is configured to be coupled to a drive shaft of a surgical tool, the drive shaft configured to move the support arm.

3. The surgical blade of claim 1, wherein the second end of the curved cutting blade is configured to be rotated through the scleral tissue of the eye in the single partial revolution of the surgical blade to make the incision.

4. The surgical blade of claim 1, wherein the curved cutting blade is configured to form the incision in the scleral tissue of approximately one and one half millimeters wide, approximately four millimeters long, and approximately four hundred microns under the anterior surface of the scleral tissue.

5. A surgical tool, comprising:
a surgical blade;
a drive shaft configured to move the surgical blade; and
a blade guide;
wherein the surgical blade comprises:
a support arm having a first end coupled to the drive shaft and a second end; and
a curved cutting blade that arcs around the first end of the support arm, the curved cutting blade having a substantially flat cross-section across its width and a curved cross-section along its length;
wherein the curved cutting blade has a first end coupled to the second end of the support arm, the curved cutting blade also having a second end configured to be moved through an anterior surface of scleral tissue of an eye without passing through a posterior surface of the scleral tissue of the eye to make an incision, the incision having a form of a scleral pocket that is capable of receiving a scleral eye implant prosthesis;
wherein the blade guide has (i) a first opening through which the second end of the curved cutting blade travels before entering the scleral tissue of the eye and (ii) a second opening through which the second end of the curved cutting blade travels after exiting the scleral tissue of the eye; and
wherein the surgical tool is configured to cause the second end of the curved cutting blade to pass through both openings during a single partial revolution of the curved cutting blade.

6. The surgical tool of claim 5, wherein the curved cutting blade is detachably coupled to the support arm.

7. The surgical tool of claim 5, wherein the drive shaft is configured to move the surgical blade through the scleral tissue of the eye by moving the support arm.

8. The surgical tool of claim 5, wherein the drive shaft is configured to provide bidirectional rotational motion to the surgical blade.

9. The surgical tool of claim 8, further comprising:
a drive motor coupled to the drive shaft, the drive motor configured to provide bidirectional rotational motion to the drive shaft; and
a receptacle coupled to the drive motor, the receptacle configured to receive electrical power from an external power source and to provide the electrical power to the drive motor.

10. The surgical tool of claim 5, further comprising a controller configured to provide first control signals for controlling the surgical blade in response to receiving second control signals.

11. The surgical tool of claim 10, further comprising a foot switch coupled to the controller through a control signal line, the foot switch configured to send the second control signals to the controller.

12. The surgical tool of claim 10, wherein one controlled movement of the surgical blade is to make the incision.

13. The surgical tool of claim 10, wherein one controlled movement of the surgical blade is to position the surgical blade to make the incision.

14. A surgical tool, comprising:
a surgical blade;
a drive shaft configured to move the surgical blade; and
a blade guide;
wherein the surgical blade comprises:
a support arm having a first end coupled to the drive shaft and a second end; and
a curved cutting blade that arcs around the first end of the support arm, the curved cutting blade having a substantially flat cross-section across its width and a curved cross-section along its length;
wherein the curved cutting blade has a first end coupled to the second end of the support arm and a second end configured to be moved through an anterior surface of scleral tissue of an eye without passing through a posterior surface of the scleral tissue of the eye to make an incision, the incision having a form of a scleral pocket that is capable of receiving a scleral eye implant prosthesis;
wherein the drive shaft is configured to move the surgical blade by causing the second end of the surgical blade to enter into the scleral tissue of the eye at a first location, travel through the scleral tissue of the eye, and exit the scleral tissue of the eye at a second location during a single partial revolution of the surgical blade;
wherein the blade guide has (i) a first opening through which the second end of the curved cutting blade travels before entering the scleral tissue of the eye and (ii) a second opening through which the second end of the curved cutting blade travels after exiting the scleral tissue of the eye; and
wherein the surgical tool is configured to cause the second end of the curved cutting blade to pass through both openings during the single partial revolution of the curved cutting blade.

15. The surgical tool of claim 14, further comprising:
a drive motor coupled to the drive shaft, the drive motor configured to provide bidirectional rotational motion to the drive shaft; and
a receptacle coupled to the drive motor, the receptacle configured to receive electrical power from an external power source and to provide the electrical power to the drive motor.

16. The surgical tool of claim 14, further comprising:
a surgical tool controller configured to receive control signals for controlling the surgical blade of the surgical tool.

17. The surgical tool of claim 16, further comprising:
a foot switch configured to send the control signals to the surgical tool controller.

18. The surgical tool of claim 14, further comprising:
an external reference line on a surface of the surgical tool, the external reference line indicating a desired location for placing the surgical tool on the eye to make the incision in the scleral tissue of the eye.

* * * * *